US010219742B2

(12) United States Patent
Dvorsky et al.

(10) Patent No.: US 10,219,742 B2
(45) Date of Patent: Mar. 5, 2019

(54) LOCATING AND ANALYZING PERFORATOR FLAPS FOR PLASTIC AND RECONSTRUCTIVE SURGERY

(75) Inventors: Peter Dvorsky, Toronto (CA); David Mark Henri Goyette, Mississauga (CA)

(73) Assignee: NOVADAQ TECHNOLOGIES ULC, Burnaby (CA)

( * ) Notice: Subject to any disclaimer, the term of this patent is extended or adjusted under 35 U.S.C. 154(b) by 0 days.

(21) Appl. No.: 12/933,477

(22) Filed: Sep. 20, 2010

(65) Prior Publication Data

US 2011/0306877 A1  Dec. 15, 2011

Related U.S. Application Data

(63) Continuation-in-part of application No. PCT/IB2009/005700, filed on Apr. 14, 2009.

(60) Provisional application No. 61/044,779, filed on Apr. 14, 2008, provisional application No. 61/243,688, filed on Sep. 18, 2009.

(51) Int. Cl.
*A61B 5/00* (2006.01)
*A61B 17/00* (2006.01)

(52) U.S. Cl.
CPC ............ *A61B 5/489* (2013.01); *A61B 5/0059* (2013.01); *A61B 5/413* (2013.01); *A61B 2017/00792* (2013.01)

(58) Field of Classification Search
USPC ........................................ 600/407, 473, 476
See application file for complete search history.

(56) References Cited

U.S. PATENT DOCUMENTS

| 4,109,647 A | 8/1978 | Stern et al. |
| 4,162,405 A | 7/1979 | Chance et al. |
| 4,200,801 A | 4/1980 | Schuresko |
| 4,263,916 A * | 4/1981 | Brooks ................. A61B 6/481 |
| | | 600/431 |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |

(Continued)

FOREIGN PATENT DOCUMENTS

| AT | 409451 B | 8/2002 |
| CA | 2212257 A1 | 8/1996 |

(Continued)

OTHER PUBLICATIONS

Pandharlpande et al. "Perfusion Imaging of the Liver: Current Challenges and Future Goals." 2005. Radiology. pp. 661-673.*

(Continued)

*Primary Examiner* — James Kish
(74) *Attorney, Agent, or Firm* — Morrison & Foerster LLP

(57) ABSTRACT

A method and an apparatus for preoperative identification of a perforator vessel for plastic and/or reconstructive surgery using ICG fluorescence angiography imaging are disclosed. Time-resolved image processing is used to highlight perforator locations and to enable visual discrimination among candidate perforators by various computed metrics. Based on these metrics, the surgeon is able to interactively locate and select perforator vessels suitable for plastic and reconstructive surgery.

20 Claims, 10 Drawing Sheets

(56) References Cited

U.S. PATENT DOCUMENTS

| | | |
|---|---|---|
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 6/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A * | 2/1995 | Flower ............... A61B 3/1241 351/205 |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A * | 7/2000 | Guracar et al. ............... 600/447 |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |

(56) References Cited

U.S. PATENT DOCUMENTS

| | | | |
|---|---|---|---|
| 6,915,154 B1* | 7/2005 | Docherty | A61B 5/0261 600/419 |
| 6,936,043 B2 | 8/2005 | Peyman | |
| 6,944,493 B2 | 9/2005 | Alam et al. | |
| 7,113,817 B1* | 9/2006 | Winchester et al. | 600/476 |
| 7,236,815 B2 | 6/2007 | Richards-Kortum et al. | |
| 7,364,574 B2 | 4/2008 | Flower | |
| 7,381,400 B2 | 6/2008 | Woltering | |
| 7,400,753 B2 | 7/2008 | Seino et al. | |
| 7,400,755 B2 | 7/2008 | West et al. | |
| 7,482,318 B2 | 1/2009 | Aurelian et al. | |
| 7,581,191 B2 | 8/2009 | Rice et al. | |
| 7,729,750 B2 | 6/2010 | Tromberg et al. | |
| 7,881,777 B2 | 2/2011 | Docherty et al. | |
| 7,885,438 B2 | 2/2011 | Uppaluri et al. | |
| 8,036,437 B2 | 10/2011 | Arditi et al. | |
| 8,073,224 B2 | 12/2011 | Strobel et al. | |
| 8,144,958 B2 | 3/2012 | Nahm et al. | |
| 8,185,176 B2 | 5/2012 | Mangat et al. | |
| 8,194,981 B2 | 6/2012 | Suzuki | |
| 8,285,353 B2 | 10/2012 | Choi et al. | |
| 8,361,775 B2 | 1/2013 | Flower | |
| 8,406,860 B2 | 3/2013 | Dvorsky et al. | |
| 8,480,579 B2 | 7/2013 | Serov et al. | |
| 8,521,260 B2 | 8/2013 | Grinvald et al. | |
| 8,538,107 B2 | 9/2013 | Röttger | |
| 8,647,605 B2 | 2/2014 | Mangat et al. | |
| 8,725,225 B2 | 5/2014 | Golijanin et al. | |
| 8,892,190 B2 | 11/2014 | Docherty et al. | |
| 8,929,974 B2* | 1/2015 | Hauger | A61B 5/0261 382/128 |
| 8,965,488 B2 | 2/2015 | Dvorsky et al. | |
| 9,089,601 B2 | 7/2015 | Golijanin et al. | |
| 9,129,366 B2 | 9/2015 | Nahm et al. | |
| RE45,916 E | 3/2016 | Golijanin et al. | |
| 9,351,644 B2 | 5/2016 | Nahm et al. | |
| 9,357,931 B2 | 6/2016 | Nahm et al. | |
| 9,421,280 B2 | 8/2016 | Mangat et al. | |
| 9,816,930 B2 | 11/2017 | Moriyama et al. | |
| 9,936,887 B2 | 4/2018 | Dvorsky et al. | |
| 2002/0025541 A1 | 2/2002 | Nelson et al. | |
| 2002/0038120 A1 | 3/2002 | Duhaylongsod et al. | |
| 2002/0099279 A1 | 7/2002 | Pfeiffer et al. | |
| 2002/0099295 A1* | 7/2002 | Gil et al. | 600/476 |
| 2002/0146369 A1 | 10/2002 | Goldenberg | |
| 2002/0181752 A1 | 12/2002 | Wallo et al. | |
| 2002/0183621 A1 | 12/2002 | Pfeiffer et al. | |
| 2003/0032885 A1 | 2/2003 | Rubinstein et al. | |
| 2003/0050543 A1 | 3/2003 | Hartmann | |
| 2003/0060718 A1 | 3/2003 | Alam et al. | |
| 2003/0060722 A1 | 3/2003 | Pfeiffer et al. | |
| 2003/0064025 A1 | 4/2003 | Yang et al. | |
| 2003/0093064 A1 | 5/2003 | Peyman | |
| 2003/0093065 A1 | 5/2003 | Peyman | |
| 2003/0156252 A1 | 8/2003 | Morris et al. | |
| 2003/0187349 A1 | 10/2003 | Kaneko et al. | |
| 2003/0232016 A1 | 12/2003 | Heinrich | |
| 2003/0236458 A1 | 12/2003 | Hochman | |
| 2004/0066961 A1* | 4/2004 | Spreeuwers et al. | 382/128 |
| 2004/0077952 A1 | 4/2004 | Rafter et al. | |
| 2004/0109231 A1 | 6/2004 | Haisch et al. | |
| 2004/0156782 A1 | 8/2004 | Alam et al. | |
| 2004/0162489 A1 | 8/2004 | Richards-Kortum et al. | |
| 2004/0171827 A1 | 9/2004 | Peng et al. | |
| 2004/0174495 A1 | 9/2004 | Levine | |
| 2005/0019744 A1 | 1/2005 | Bertuglia | |
| 2005/0020891 A1 | 1/2005 | Rubinstein et al. | |
| 2005/0033145 A1 | 2/2005 | Graham et al. | |
| 2005/0069525 A1 | 3/2005 | Mikael | |
| 2005/0089866 A1 | 4/2005 | Hinuma et al. | |
| 2005/0107380 A1 | 5/2005 | Nimmo et al. | |
| 2005/0142556 A1 | 6/2005 | Hoon et al. | |
| 2005/0182321 A1 | 8/2005 | Frangioni | |
| 2005/0182327 A1 | 8/2005 | Petty et al. | |
| 2005/0182431 A1 | 8/2005 | Hausen et al. | |
| 2005/0182434 A1 | 8/2005 | Docherty et al. | |
| 2005/0187477 A1 | 8/2005 | Serov et al. | |
| 2005/0197583 A1 | 9/2005 | Chance | |
| 2005/0254008 A1 | 11/2005 | Ferguson et al. | |
| 2006/0013768 A1 | 1/2006 | Woltering | |
| 2006/0079750 A1 | 4/2006 | Fauci et al. | |
| 2006/0108509 A1 | 5/2006 | Frangioni et al. | |
| 2006/0118742 A1 | 6/2006 | Levenson et al. | |
| 2006/0147897 A1 | 7/2006 | Grinvald et al. | |
| 2006/0239921 A1 | 10/2006 | Mangat et al. | |
| 2006/0241499 A1 | 10/2006 | Irion et al. | |
| 2007/0122344 A1 | 5/2007 | Golijanin | |
| 2007/0122345 A1 | 5/2007 | Golijanin | |
| 2007/0203413 A1 | 8/2007 | Frangioni | |
| 2007/0254276 A1 | 11/2007 | Deutsch et al. | |
| 2008/0007733 A1 | 1/2008 | Marks et al. | |
| 2008/0015446 A1* | 1/2008 | Mahmood et al. | 600/476 |
| 2008/0025918 A1* | 1/2008 | Frangioni | A61K 49/0004 424/9.6 |
| 2008/0044073 A1 | 2/2008 | Bernhardt et al. | |
| 2008/0071176 A1 | 3/2008 | Docherty et al. | |
| 2008/0161744 A1 | 7/2008 | Golijanin et al. | |
| 2008/0221421 A1 | 9/2008 | Choi et al. | |
| 2008/0221648 A1 | 9/2008 | Flower | |
| 2008/0239070 A1 | 10/2008 | Westwick et al. | |
| 2008/0319309 A1 | 12/2008 | Bredno et al. | |
| 2009/0005693 A1 | 1/2009 | Brauner et al. | |
| 2009/0042179 A1 | 2/2009 | Peltie et al. | |
| 2009/0048516 A1 | 2/2009 | Yoshikawa et al. | |
| 2009/0054788 A1 | 2/2009 | Hauger et al. | |
| 2009/0118623 A1 | 5/2009 | Serov et al. | |
| 2009/0137902 A1 | 5/2009 | Frangioni et al. | |
| 2009/0252682 A1 | 10/2009 | Hillman | |
| 2009/0297004 A1 | 12/2009 | Baumgart | |
| 2010/0022898 A1 | 1/2010 | Rubinstein et al. | |
| 2010/0036217 A1* | 2/2010 | Choi et al. | 600/317 |
| 2010/0061604 A1* | 3/2010 | Nahm | G06T 7/0014 382/128 |
| 2010/0222673 A1 | 9/2010 | Mangat et al. | |
| 2010/0286529 A1 | 11/2010 | Carroll et al. | |
| 2011/0001061 A1 | 1/2011 | Ishihara | |
| 2011/0013002 A1 | 1/2011 | Thompson et al. | |
| 2011/0063427 A1 | 3/2011 | Fengler et al. | |
| 2011/0071403 A1 | 3/2011 | Sevick-Muraca et al. | |
| 2011/0090325 A1* | 4/2011 | Hauger | A61B 5/0261 348/77 |
| 2011/0098685 A1 | 4/2011 | Flower | |
| 2012/0026325 A1 | 2/2012 | Bunker et al. | |
| 2012/0078093 A1 | 3/2012 | Flower | |
| 2012/0165662 A1 | 6/2012 | Nahm et al. | |
| 2013/0217985 A1 | 8/2013 | Dvorsky et al. | |
| 2013/0230866 A1 | 9/2013 | Miyashita et al. | |
| 2013/0245456 A1 | 9/2013 | Ferguson, Jr. et al. | |
| 2013/0286176 A1 | 10/2013 | Westwick et al. | |
| 2013/0296715 A1 | 11/2013 | Lasser et al. | |
| 2013/0345560 A1 | 12/2013 | Ferguson, Jr. et al. | |
| 2014/0099007 A1 | 4/2014 | Sarkar et al. | |
| 2014/0308656 A1 | 10/2014 | Flower | |
| 2014/0316262 A1 | 10/2014 | Havens | |
| 2015/0112192 A1 | 4/2015 | Docherty et al. | |
| 2015/0112193 A1 | 4/2015 | Docherty et al. | |
| 2015/0196208 A1 | 7/2015 | Dvorsky et al. | |
| 2015/0230710 A1 | 8/2015 | Nahm et al. | |
| 2015/0230715 A1 | 8/2015 | Nahm et al. | |
| 2016/0038027 A1 | 2/2016 | Brzozowski et al. | |
| 2016/0110870 A1 | 4/2016 | Moriyama et al. | |
| 2016/0199515 A1 | 7/2016 | Flower | |
| 2016/0371834 A1 | 12/2016 | Watanabe et al. | |
| 2017/0039710 A1 | 2/2017 | Minai et al. | |
| 2017/0303800 A1 | 10/2017 | Flower et al. | |
| 2018/0020933 A1 | 1/2018 | Dvorsky et al. | |
| 2018/0104362 A1 | 4/2018 | Golijanin et al. | |

FOREIGN PATENT DOCUMENTS

| | | |
|---|---|---|
| CA | 2413033 A1 | 3/2000 |
| CA | 2711560 A1 | 7/2009 |
| CN | 1049781 A | 3/1991 |
| CN | 1200174 A | 11/1998 |

(56) References Cited

FOREIGN PATENT DOCUMENTS

| | | |
|---|---|---|
| CN | 1399528 A | 2/2003 |
| CN | 101264014 A | 9/2008 |
| DE | 39 06 860 A1 | 9/1989 |
| DE | 19608027 A1 | 9/1996 |
| DE | 10028233 A1 | 1/2002 |
| DE | 101 20 980 A1 | 11/2002 |
| DE | 69727220 T2 | 12/2004 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0826335 A1 | 3/1998 |
| EP | 1 761 171 A2 | 3/2007 |
| EP | 1874181 A1 | 1/2008 |
| GB | 2203831 A | 10/1988 |
| JP | S58-222331 A | 12/1983 |
| JP | S59-069721 A | 4/1984 |
| JP | S59-070903 A | 4/1984 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | 9-308609 A | 12/1997 |
| JP | H09-309845 A | 12/1997 |
| JP | H10-503480 A | 3/1998 |
| JP | 10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2002-219129 A | 8/2002 |
| JP | 2003-510121 A | 3/2003 |
| JP | 2003-144401 A | 5/2003 |
| JP | 2004-528917 A | 9/2004 |
| JP | 2006-503620 A | 2/2006 |
| JP | 2006-192280 A | 7/2006 |
| JP | 2007-21006 A | 2/2007 |
| JP | 3896176 B2 | 3/2007 |
| JP | 2008-525126 A | 7/2008 |
| JP | 2008-535600 A | 9/2008 |
| JP | 2008-231113 | 10/2008 |
| JP | 2010-505582 A | 2/2010 |
| JP | 2011-509768 A | 3/2011 |
| JP | 2011-519589 A | 7/2011 |
| JP | 5918532 B2 | 5/2016 |
| KR | 90-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO-1993/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | 01/08552 A1 | 2/2001 |
| WO | WO-2001/17561 A1 | 3/2001 |
| WO | 01/22870 A1 | 4/2001 |
| WO | WO-2001/22870 A1 | 4/2001 |
| WO | WO-2001/39764 A2 | 6/2001 |
| WO | WO-2001/69244 A2 | 9/2001 |
| WO | 01/80734 A1 | 11/2001 |
| WO | 01/82786 A2 | 11/2001 |
| WO | WO-2002/061390 A2 | 8/2002 |
| WO | WO-2003/006658 A1 | 1/2003 |
| WO | WO-2004/006963 A1 | 1/2004 |
| WO | 20041052195 A1 | 6/2004 |
| WO | WO 2004/052195 A1 | 6/2004 |
| WO | WO-2005/026319 A2 | 3/2005 |
| WO | WO-2005/034747 A1 | 4/2005 |
| WO | 2005/079238 A2 | 9/2005 |
| WO | WO-2006/111836 A1 | 10/2006 |
| WO | WO-2006/111909 A1 | 10/2006 |
| WO | 20061123742 A1 | 11/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2007/028032 A2 | 3/2007 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | 20091048660 A2 | 4/2009 |
| WO | WO-2009/046985 A2 | 4/2009 |
| WO | WO-2009/046985 A3 | 4/2009 |
| WO | 20091092162 A1 | 7/2009 |
| WO | 20091127972 A2 | 10/2009 |
| WO | WO-2012/038824 A1 | 3/2012 |
| WO | WO-2012/096878 A2 | 7/2012 |
| WO | WO-2013/190391 A2 | 12/2013 |

OTHER PUBLICATIONS

Holm et al., "Monitoring Free Flaps Using Laser-Indeuced Fluorescence of Indocyanine Green: A Preliminary Experience." 2002. Wiley InterScience, pp. 278-287.*

Holm et al., "Laser-Induced Fluorescence of Indocyanine Green: Plastic Surgical Applications." 2003. European Journal of Plastic Surgery, vol. 26, pp. 19-25.*

PR Newswire, "Novadaz Imaging System Receives FDA Clearance for use During Plastic Reconstructive Surgery," Jan. 29, 2007, 3 pages.*

Newman et al., "Update on the Application of Laser-Assisted Indocyanine Green Fluorescent Dye Angiography in Microsurgical Breast Reconstruction," Oct. 31, 2009, 2 pages.*

Azuma et al., "Detection of Skin Perforators by Indocyanine Green Fluorescence Nearly Infrared Angiography," published 2008, presented in part Jun. 2007, pp. 1062-1067.*

Verbeek, X., "High-Resolution Functional Imaging With Ultrasound Contrast Agents Based on RF Processing in an In Vivo Kidney Experiment", Ultrasound in Med. & Biol., vol. 27, No. 2, pp. 223-233, 2001.

(56) References Cited

OTHER PUBLICATIONS

Translation of Chinese Office Action dated Jul. 3, 2012, issued in counterpart Chinese Application No. 200980123414.0.
Translation of Russian Office Action dated Mar. 29, 2013, issued in counterpart Russian Application No. 2011111078/14.
Chinese Office Action dated May 23, 2013, issued in counterpart Chinese Application No. 200980123414.0.
Mexican Office Action dated May 30, 2013, issued in counterpart Mexican Application No. MX/a/2010/011249.
Japanese Office Action dated Jul. 30, 2013, issued in counterpart Japanese Application No. 2011-504574.
Translation of Russian Decision on Grant dated Jul. 29, 2013, issued in counterpart Russian Application No. 2011111078/14.
Supplemental European Search Report and Written Opinion issued in EP 09 732 993.2 dated May 15, 2014.
Iiolm et al., "Intraoperative evaluation of skin-flap viability using laser-induced fluorescence of indocyanine green", British Journal of Plastic Surgery, Churchill Livingstone, Great Britain, vol. 55, No. 8, Dec. 1, 2002, pp. 635-644.
Krishnan K. G. et al., "The role of near-infrared angiography in the assessment of post-operative venous congestion in random pattern, pedicled island and free flaps", British Journal of Plastic Surgery, Churchill Livingston, Great Britain, vol. 58, No. 3, Apr. 1, 2005, pp. 330-338.
Frenzel H. et al., "In vivo perfusion analysis of normal and dysplastic ears and its implication on total auricular reconstruction", Journal of Plastic, Reconstructive and Aesthetic Surgery, Churchill Livingstone, Great Britain, vol. 61, Apr. 18, 2008, pp. S21-S28.
Detter, C. et al. "Fluorescent Cardiac Imaging: A Novel Intraoperative Method for Quantitative Assessment of Myocardial Perfusion During Graded Coronary Artery Stenosis." Aug. 1, 2007, pp. 1007-1014, vol. 116, No. 9.
Detter, C. et al. "Near-Infrared Fluorescence Coronary Angiography: A New Noninvasive Technology for Intraoperative Graft Patency Control." The Heart Surgery Forum, Jun. 2011, pp. 364-369, vol. 5, Issue 4.
Forrester et al. "Comparison of Laser Speckle and Laser Doppler Perfusion Imaging: Measurement in Human Skin and Rabbit Artivular Tissue." Medical and Biological Engineering and Computing, Nov. 1, 2002. pp. 687-697, vol. 40, No. 6.
Jolion, J. et al. "Robust Clustering with Applications in Computer Vision." IEEE Transactions on Pattern Analysis and Machine Intelligence, Aug. 1991, pp. 791-802, vol. 13, No. 8.
Martinez-Perez, M. et al. "Unsupervised Segmentation Based on Robust Estimation and Cooccurrence Data." Proceedings of the International Conference on Miage Processing (ICIP) Lausanne, Sep. 19, 1996, pp. 943-945, vol. 3.
Sezgin, M. et al. "Survey over image thresholding techniques and quantitative performance evaluation." Journal of Electronic Imaging, Jan. 2004, pp. 146-165, vol. 13(1).
Yamaguchi et al. "Evaluation of Skin Perfusion After Nipple-Sparing Mastectomy by Indocyanine Green Dye." (With English Abstract) Journal of Saitama Medical University, Japan, Apr. 2005, pp. 45-50, vol. 32.
Jan. 25, 2012 International Search Report issued in Application No. PCT/IB11/002381.
Chinese Office Action dated Nov. 12, 2015, for Chinese Patent Application No. 201180057244.8, filed on Sep. 20, 2010, five pages.
European Office Action dated Mar. 27, 2015, for EP Application No. 09 732 993.2, filed on Apr. 14, 2008, six pages.
Extended European Search Report dated Feb. 22, 2012, for EP Application No. 09 704 642.9, filed on Jan. 25, 2008, fifteen pages.
Extended European Search Report dated Apr. 28, 2014, for EP Application No. 09 732 993.2, filed on Apr. 14, 2008, eight pages.
Extended European Search Report dated Jan. 28, 2014, for EP Application No. 11 826 475.3, filed on Sep. 20, 2010, six pages.
International Search Report dated Jun. 8, 2009, for PCT Patent Application No. PCT/CA2009/000073, filed on Jan. 23, 2009, three pages.
International Search Report dated Dec. 3, 2009, for PCT Patent Application No. PCT/162009/005700, filed on Apr. 14, 2009, three pages.
Japanese Office Action dated Sep. 14, 2015, for Japanese Patent Application No. 2011-504574, filed on Apr. 14, 2009, five pages.
Korean Office Action dated Nov. 30, 2015, for Korean Patent Application No. 10-2010-7024977, filed on Apr. 14, 2009, two pages.
Notice of Allowance dated Oct. 18, 2012, for U.S. Appl. No. 12/841,659, filed Jul. 22, 2010, seven pages.
Notice of Allowance date Aug. 7, 2014, for U.S. Appl. No. 13/850,063, filed Mar. 25, 2013, nine pages.
Notice of Allowance dated Oct. 16, 2014, for U.S. Appl. No. 13/850,063, filed Mar. 25, 2013, eight pages.
Notice of Allowance dated Nov. 25, 2015, for U.S. Appl. No. 14/598,832, filed Jan. 16, 2015, seven pages.
Notice of Allowance dated Oct. 29, 2015, for EP Application No. 09 704 642.9, filed on Jan. 25, 2008, two pages.
Notice of Allowance dated Oct. 21, 2015, for EP Application No. 11 826 475.3, filed on Sep. 20, 2010, eight pages.
Written Opinion of the International Searching Authority dated Jun. 8, 2009, for PCT Patent Application No. PCT/CA2009/000073, filed on Jan. 23, 2009, four pages.
Written Opinion of the International Searching Authority dated Dec. 3, 2009, for PCT Patent Application No. PCT/IB2009/005700, filed on Apr. 14, 2009, six pages.
Written Opinion of the International Searching Authority dated Feb. 1, 2012, for PCT Patent Application No. PCT/IB2011/002381, filed on Sep. 20, 2011, four pages.
Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience Methods* 45(1-2):15-22.
Alander, J.T. et al. (Jan. 1, 2012). "A Review of Indocyanine Green Fluorescent Imaging in Surgery," *International Journal of Biomedical Imaging* 2012:1-26, article ID 940585.
Alfano et al. (Oct. 1987). "Fluorescence Spectra from Cancerous and Normal Human Breast and Lung Tissues," *IEEE Journal of Quantum Electronics* QE-23(10):1806-1811.
Alm, A. et al. (Jan. 1, 1973). "Ocular and Optic Nerve Blood Flow at Normal and Increased Intraocular Pressures in Monkeys (*Macaca irus*): A Study with Radioactively Labelled Microspheres Including Flow Determinations in Brain and Some Other Tissues," *Experimental Eye Research* 15(1):15-29.
Alonso-Burgos, A. et al.(2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.
Alvarez, F. J. et al. (Apr. 1996). "Behaviour of Isolated Rat and Human Red Blood Cells Upon Hypotonic-Dialysis Encapsulation of Carbonic Anhydrase and Dextran," *Biotechnology and Applied Biochemistry* 23(2):173-179.
Ancalmo, N. et al. (1997). "Minimally invasive coronary artery bypass surgery: really minimal?" *Ann. Thorac. Surg.* 64:928-929.
Andersson-Engels, S. et al. (1991). "Fluorescence Characteristics of Atherosclorotic Plaque and Malignant Tumors," in *Optical Methods for Tumor Treatment and Early Diagnosis: Mechanisms and Techniques*, T. J. Dougherty (Ed.), The Society of Photo-optical Instrumentation Engineers (SPIE) 1426:31-43, fourteen pages.
Andersson-Engels, S. et al. (Mar. 1989). "Tissue Diagnostics Using Laser-Induced Fluorescence," *Berichte der Bunsengesellschaft für physikalische Chemie* 93(3):335-342.
Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.
Annese, V. et al. (2005). "RBCs-Mediated Delivery of Dexamethasone in Steroid-Dependent IBD Patients-a Pilot Uncontrolled Study," *American Journal of Gastroenterol.* 100:1370-1375.
Argus-50/CA, Inter cellular CA2+ (calcium ion) Image Analysis system (Feb. 1992). "Observation and 2-dimensional analysis of

(56) References Cited

OTHER PUBLICATIONS

Ca2+ concentration distribution. Fura-2 and Indo-1 compatible. Ca2+ concentrations are calculated from the fluorescence ratio," pp. 1-10.

Author Unknown. (Jun. 4, 2008)."Invitrogen," Material Safety Data Sheet, p. 1-4.

Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.

Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.

Barton, J.K. et al. (1999) "Simultaneous irradiation and imaging of blood vessels during pulsed laser delivery," *Lasers in Surgery and Medicine* 24(3):236-243.

Bassingthwaighte, J.B. et al. (Apr. 1974). "Organ Blood Flow, Wash-in, Washout, and Clearance of Nutrients and Metabolites," *Mayo Clin. Proc.* 49(4):248-255.

Batliwala, H. et al. (Apr. 15, 1995). "Methane-Induced Haemolysis of Human Erythrocytes," *Biochemical J.* 307(2):433-438.

Bek, T. (1999). "Diabetic Maculopathy Caused by Disturbances in Retinal Vasomotion: A New Hypothesis," *Acta Ophthalmologica Scandinavica* 77:376-380.

Benson, R.C. et al. (1978). "Fluorescence Properties of Indocyanine Green as Related to Angiography," *Phys. Med. Biol.* 23(1):159-163.

Black's Medical Dictionary, "Perfusion," 42nd Edition (2009), two pages.

Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.

Boldt, .J. et al. (Feb. 1990). "Lung management during cardiopulmonary bypass: influence on extravascular lung water," *Journal of Cardiothoracic Anesthesia* 4(1):73-79.

Boldt, J. et al. (1991). "Does the technique of cardiopulmonary bypass affect lung water content?" *European Journal of Cardio-Thoracic Surgery* 5:22-26.

Bütter, A. et al. (May 2005). "Melanoma in Children and the Use of Sentinel Lymph Node Biopsy," *Journal of Pediatric Surgery* 40(5):797-800.

C2741, Compact High Performance video camera for industrial applications with Built-in contrast enhancement circuit, Jun. 1998; 6 pages.

Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.

Coffey, J.H. et al. (1984). "Evaluation of Visual Acuity During Laser Photoradiation Therapy of Cancer," *Lasers in Surgery and Medicine* 4(1):65-71.

Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.

Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.

Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.

Dail, W.G. et al. (Oct. 1999). "Multiple Vasodilator Pathways from the Pelvic Plexus to the Penis of the Rat," *International Journal of Impotence Research* 11(5):277-285.

Dan, a.G. et al. (Nov. 2004). "1% Lymphazurin vs 10% Fluorescein for Sentinel Node Mapping in Colorectal Tumors," *Arch Surg.* 139(11):1180-1184.

Daniels, G. et al. (Apr. 2007). "Towards Universal Red Blood Cell," *Nature Biotechnology* 25(4):427-428.

De Flora, A. (Sep. 1986). "Encapsulation of Adriamycin in human erythrocytes," *Proc. Natl. Acad. Sci., USA* 83(18):7029-7033.

De-Grand, A.M. et al. (Dec. 2003). "An Operational Near Infrared Fluorescence Imaging System Prototype for Large Animal Surgery," *Technology in Cancer Research & Treatment* 2(6):1-10.

Deloach, J.R. (ed.) et al. (1985). *Red Blood Cells as Carriers for Drugs. A Method for Disseminating Chemotherapeutics, Hormones, Enzymes and Other Therapeutic Agents via the Circulatory System*, Karger, Basel, CH, pp. v-vii, (Table of Contents).

Deloach, J.R. (Jun. 1983). "Encapsulation of Exogenous Agents in Erythrocytes and the Circulating Survival of Carrier Erythrocytes," *Journal of Applied Biochemistry* 5(3):149-157.

Demos (May/Jun. 2004). "Near-Infrared Autofluorescence Imaging for Detection of Cancer," *Journal of Biomedical Optics* 9(3):587-592.

Desai, N.D. et al. (Oct. 18, 2005, e-published on Sep. 28, 2005) "Improving the Quality of Coronary Bypass Surgery with Untraoperative Angiography," *Journal of the American College of Cardiology* 46(8):1521-1525.

Dietz, F.B. et al. (Feb. 2003). "Indocyanine Green: Evidence of Neurotoxicity in Spinal Root Axons," *Anesthesiology* 98(2):516-520.

Digital CCD Microscopy (date unknown). Chapter 14, pp. 259-282.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed CMOS-Camera," in *Novel Optical Instrumentation for Biomedical Applications III*, C. Depeursinge, ed., Proceedings of SPIE-OSA Biomedical Optics (Optical Society of America, 2007), SPIE-OSA, 6631:0N1-0N7, nine pages.

Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.

Flower, R.W. (1992). "Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

Flower, R.W. (Dec. 1973). "Injection Technique for Indocyanine Green and Sodium Fluorescein Dye Angiography of the Eye," *Investigative Opthamology* 12(12):881-895.

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," *Investigative Ophthalmology, & Visual Science* 49(12):5510-5516.

Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).

(56) References Cited

OTHER PUBLICATIONS

Frangioni, J.V. (Oct. 2003). "In Vivo Near-Infrared Fluorescence Imaging," *Current Opinion in Chemical Biology* 7(5):626-634.
Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.
Gagnon, A.R. et al. (2006). "Deep and superficial inferior epigastric artery perforator flaps," *Cirugia Plástica Ibero-Latinoamericana* 32(4):7-13.
Gardner, T.J. (1993). "Coronary artery disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.
Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.
Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal Of Physical Chemistry A* 107(18):3443-3449.
Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.
Giunta, R.E. et al. (Jul. 2005). "Prediction of Flap Necrosis with Laser Induced Indocyanine Green Fluorescence in a Rat Model," *British Journal of Plastic Surgery* 58(5):695-701.
Giunta, R.E. et al. (Jun. 2000). "The Value of Preoperative Doppler Sonography for Planning Free Perforator Flaps," *Plastic and Reconstructive Surgery* 105(7):2381-2386.
Glossary, Nature, downloaded from the internet <http://www.nature.com/nrg/journal/v4/nl0/glossary/nrgl 183_glossary.html>> HTML on Jun. 30, 2014; 3 pages.
Glover, J.C. et al. (Nov. 1986). "Fluorescent Dextran-Amines Used as Axonal Tracers in the Nervous System of the Chicken Embryo," *Journal of Neuroscience Methods* 18(3):243-254.
Goldstein, J.A. et al. (Dec. 1998). "Intraoperative Angiography to Assess Graft Patency After Minimally Invasive Coronary Bypass," *Ann. Thorac. Surg.* 66(6):1978-1982.
Gothoskar A.V. (Mar. 2004). "Resealed Erythrocytes: A Review," *Pharmaceutical Technology* pp. 140, 142, 144, 146, 148, 150, 152 and 154-158, twelve pages.
Granzow, J.W. et al. (Jul. 2007)."Breast Reconstruction with Perforator Flaps" *Plastic and Reconstructive Surgery* 120(1):1-12.
Green, H.A. et al. (Jan. 1992). "Burn Depth Estimation Using Indocyanine Green Fluorescence," *Arch Dermatol* 128(1):43-49.
Haglund, M. et al. (Feb. 1996). "Enhanced Optical Imaging of Human Gliomas and Tumor Margins," *Neurosurgery* 38(2):308-317.
Haglund, M.M. et al. (Nov. 1994). "Enhanced Optical Imaging of Rat Gliomas and Tumor Margins," *Neurosurgery* 35(5):930-941.
Hallock, G.G. (Jul. 2003). "Doppler sonography and color duplex imaging for planning a perforator flap," *Clinics in Plastic Surgery* 30(3):347-357.
Hamamatsu Brochure. (May 1997). Specifications for Real-time Microscope Image Processing System: ARGUS-20 with C2400-75i; 4 pages.
Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.
Hayata, Y. et al. (Jul. 1982). "Fiberoptic Bronchoscopic Laser Photoradiation for Tumor Localization in Lung Cancer," *Chest* 82(1):10-14.
He, Z. (Feb. 2009). "Fluorogold Induces Persistent Neurological Deficits and Circling Behavior in Mice Over-Expressing Human Mutant Tau," *Current Neurovascular Research* 6(1):54-61.

Herts, B.R. (May 2003). "Imaging for Renal Tumors," *Current Opin. Urol.* 13(3):181-186.
Hirano et al. (1989). "Photodynamic Cancer Diagnosis and Treatment System Consisting of Pulse Lasers and an Endoscopic Spectro-Image Analyzer," *Laser in Life Sciences* 3(2):99-116.
Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.
Hung, J. et al. (1991). "Autofluorescence of Normal and Malignant Bronchial Tissue," *Lasers in Surgery and Medicine* 11(2):99-105.
Ikeda, S. (Jul. 1989). "Bronichial Telivision Endoscopy," *Chest* 96(1):41S-42S.
Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.
Jagoe, J.R. et al. (1989). "Quantification of retinal damage during cardiopulmonary bypass," Third International Conference on Image Processing and its Applications (Conf. Publ. No. 307), IEE, pp. 319-323.
Jamis-Dow, C.A. et al. (Mar. 1996). "Small (< or = 3-cm) Renal Masses: Detection with CT versus US and Pathologic Correlation," *Radiology* 198(3):785-788.
Kamolz, L.-P. et al. (Dec. 2003). "Indocyanine Green Video Angiographies Help to Identify Burns Requiring Operation," *Burns* 29(8):785-791.
Kapadia, C.R. et al. (Jul. 1990). "Laser-Induced Fluorescence Spectroscopy of Human Colonic Mucosa. Detection of Adenomatous Transformation," *Gastroenterology* 99(1):150-157.
Kato, H. et al. (Jun. 1985). "Early Detection of Lung Cancer by Means of Hematoporphyrin Derivative Fluorescence and Laser Photoradiation," *Clinics in Chest Medicine* 6(2):237-253.
Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.
Keon, W.J. et al. (Dec. 1979). "Coronary Endarterectomy: An Adjunct to Coronary Artery Bypass Grafting," *Surgery* 86(6):859-867.
Kim, S. et al. (2004, e-published Dec. 7, 2003). "Near-Infrared Fluorescent Type II Quantum Dots for Sentinel Lymph Node Mapping," *Nature Biotechnology* 22(1):93-97.
Kim, S.G. et al. (Jun. 15, 1988). "Quantitative Determination of Tumor Blood Flow and Perfusion Via Deuterium Nuclear Magnetic Resonance Spectroscopy in Mice," *Cancer Res.* 48(12):3449-3453.
Kiryu, J. et al. (Sep. 1994). "Noninvasive Visualization of the Choriocapillaris and its Dynamic Filling," *Investigative Ophthalmology & Visual Science* 35(10):3724-3731.
Kitai, T. et al. (Jul. 2005). "Fluorescence Navigation with Indocyanine Green for Detecting Sentinel Lymph Nodes in Breast Cancer," *Breast Cancer* 12(3):211-215.
Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.
Köbbert, C. et al. (Nov. 2000). "Current Concepts in Neuroanatomical Tracing," *Progress in Neurobiology* 62(4):327-351.
Kokaji, K. et al. (Date Unknown). "Intraoperative Quality Assessment by Using Fluorescent Imaging in Off-pump Coronary Artery Bypass Grafting," *The Department of Cardiovascular Surgery, University of Keio*, Tokyo, Japan. (Abstract only).
Kömürcü, F. et al. (Feb. 2005). "Management Strategies for Peripheral Iatrogenic Nerve Lesions," *Annals of Plastic Surgery* 54(2):135-139.
Kuipers, J.A. et al. (1999). "Recirculatory and Compartmental Pharmacokinetic Modeling of Alfentanil Pigs, the Influence of Cardiac Output," *Anesthesiology* 90(4)1146-1157.
Kupriyanov, V.V. et al. (Nov. 2004). "Mapping Regional Oxygenation and Flow in Pig Hearts In Vivo Using Near-infrared Spectroscopic Imaging," *Journal of Molecular and Cellular Cardiology* 37(5):947-957.
Kurihara, K. et al. (Jun. 1984). "Nerve Staining with Leucomethylene Blue: An Experimental Study," *Plastic and Reconstruction Surgery* 73(6):960-964.

(56) References Cited

OTHER PUBLICATIONS

Kyo, S. "Use of Ultrasound Cardiology during Coronary Artery Bypass Surgery," *Heart and Blood Vessel Imaging II*; 3 pages.
Lam, S. et al. (1991). "Mechanism of Detection of Early Lung Cancer by Ratio Fluorometry," *Lasers in Life Sciences* 4(2):67-73.
Lam, S. et al. (Feb. 1990). "Detection of Early Lung Cancer Using Low Dose Photofrin II," *Chest* 97(2):333-337.
Lam, S. et al. (Jul. 1, 1990). "Detection of Lung Cancer by Ratio Fluorometry With and Without Photofrin II," *Proc. SPIE—Optical Fibers in Medicine V* 1201:561-568.
Lam, S. et al. (Nov. 1-4, 1990). "Fluorescence Imaging of Early Lung Cancer," *Annual International Conference of the IEEE Engineering in Medicine and Biology Society* 12(3):1142-1143.
Lam, S.C. et al. (1993). "Fluorescence Detection," Chapter 20 in *Lung Cancer Roth*, J.A.(ed.), et al., Blackwell Scientific Publications Inc., 238 Main Street, Cambridge, Massachusetts, 02142, pp. 325-338, sixteen pages.
Lanciego, J.L. et al. (Jun. 1998). "Multiple Neuroanatomical Tracing in Primates," *Brain Research Protocols* 2(4):323-332.
Lanciego, J.L. et al. (Oct. 1998). "Multiple Axonal Tracing: Simultaneous Detection of Three Tracers in the Same Section," *Histochemistry and Cell Biology* 110(5):509-515.
Laub, G.W. et al. (Nov. /Dec. 1989). "Experimental Use of Fluorescein for Visualization of Coronary Arteries," *Vascular and Endovascular Surgery* 23(6):454-457.
Lee, E.T. et al. (Mar. 1997). "A New Method for Assessment of Changes in Retinal Blood Flow," *Mecial Engineering & Physics* 19(2):125-130.
Leissner, J. et al. (Jan. 2004). "Extended Radical Lymphadenectomy in Patients with Urothelial Bladder Cancer: Results of a Prospective Multicenter Study," *The Journal of Urology* 171(1):139-144.
Leithner, "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/dissertationen/leith_ner-ch_ristoph-2003-07-14/> [English Abstract and Machine Translation].
Liedberg et al. (2003). "Sentinel-Node-Diagnostik Beim Invasiven (Bladder Cancer and the Sentinel Node Concept)," *Aktuel Urol.* 34:115-118 (English Abstract Only).
Liedberg, F. et al. (Jan. 2006). "Intraoperative Sentinel Node Detection Improves Nodal Staging in Invasive Bladder Cancer," *The Journal of Urology* 175(1):84-89.
Lippincott's New Medical Dictionary. "Perfusion," p. 707 (1897), three pages.
Liptay, M.J. (Mar. 2004). "Sentinel Node Mapping in Lung Cancer," *Annals of Surgical Oncology* 11(Supplement 3):271S-274S.
Liu Q. P. et al. (Apr. 2007). "Bacterial Glycosidases for the Production of Universal Red Blood Cells" *Nature Biotechnology* 25(7):454-464.
Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.
Mack, M.J. et al. (Sep. 1998). "Arterial Graft Patency in Coronary Artery Bypass Grafting: What Do We Really Know?," *Ann. Thorac. Surg.* 66(3):1055-1059.
Magnani, M. et al. (Aug. 1998). "Erythrocyte Engineering for Drug Delivery and Targeting," *Biotechnology and Applied Biochemistry* 28(Part 1):1-6.
Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.
Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.
Marangos, N. et al. (Dec. 2001). "In Vivo Visualization of the Cochlear Nerve and Nuclei with Fluorescent Axonal Tracers," *Hearing Research* 162(1-2):48-52.
May, S. (May/Jun. 1995). "Photonic Approaches to Burn Diagnostics," *Biophotonics International* pp. 44-50.
McKee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.
Merriam Webster Medline Plus Medical Dictionary. "Perfusion," located at http://www.merriam-webster.com/medlineplus/perfusion, last visited on Apr. 15, 2015, one page.
Microscope Video Camera, for Fluorescent Observation, Easy Fluorescent Image Analysis a CCD Camera; 7 pages.
Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.
Mitaka USA, Inc. (2015). "PDE Breast Free Flap Evaluation," located at <http://mitakausa.com/category/pde_education/flaps/>, last visited on Dec. 29, 2015, four pages.
Mitaka USA, Inc. (2015). "PDE-Neo" located at <http://mitakausa.com/pde-neo/>, last visited on Dec. 29, 2015, two pages.
Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.
Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.
Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-24.
Motomura et al. (1999). "Sentinel Node Biopsy Guided by Indocyanine Green Dye in Breast Cancer Patients," *Japan J. Clin. Oncol.* 29(12):604-607.
Mullooly, V.M. et al. (1990). "Dihematoporphyrin Ether-Induced Photosensitivity in Laryngeal Papilloma Patients," *Lasers in Surgery and Medicine* 10(4):349-356.
Murphy (2001). "Digital CCD Microscopy," Chapter 14 in *Fundamentals of Light Microscopy and Electronic Imaging*, John Wiley and Sons, pp. i-xi and 259-281.
Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.
Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366.
Nakayama, A. et al. (Oct. 2002). "Functional Near-Infrared Fluorescence Imaging for Cardiac Surgery and Targeted Gene Therapy," *Molecular Imaging* 1(4):365-377.
Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.
Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.
Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.
Ogata, F. et al. (Jun. 2007). "Novel Lymphography Using Indocyanine Green Dye for Near-Infrared Fluorescence Labeling," *Annals of Plastic Surgery* 58(6):652-655.

(56) References Cited

OTHER PUBLICATIONS

Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.

Ooyama, M. (Oct. 12-15, 1994). The 8th Congress of International YAG Laser Symposium, The 15th Annual Meeting of Japan Society for Laser Medicine, Sun Royal Hotel, Japan.

Ott, P. "Hepatic Elimination of Indocyanine Green with Special Reference to Distribution Kinetics and the Influence of Plasma Protein Binding," Thesis; 47 pages.

Oxford Concise Medical Dictionary. "Perfusion," p. 571 (1980), three pages.

Pagni, S. et al. (Jun. 1997). "Anastomotic Complications in Minimally Invasive Coronary Bypass Grafting," *Ann. Thorac. Surg.* 63(6 Suppl):S64-S67.

Palcic et al. (1991). "Lung Imaging Fluorescence Endoscope: A Device for Detection of Occult Lung Cancer," *Medical Design and Material*, thirteen pages.

Palcic, B. et al. (1990). "Development of a Lung Imaging Fluorescence Endoscope," *Annual International Conference of the IEEE Engineering in Medicine and Biology Society* 12(1):0196-0197.

Palcic, B. et al. (Aug. 1, 1990). "The Importance of Image Quality for Computing Texture Features in Biomedical Specimens," *Proc. SPIE* 1205:155-162.

Palcic, B. et al. (Jun. 1, 1991). "Lung Imaging Fluorescence Endoscope: Development and Experimental Prototype," *Proc. SPIE* 1448:113-117.

Palcic, B. et al. (Mar. 1991). "Detection and Localization of Early Lung Cancer by Imaging Techniques," *Chest* 99(3):742-743.

Paques, M. et al. (Mar. 2003). "Axon-Tracing Properties of Indocyanine Green," *Arch Ophthalmol.* 121(3):367-370.

Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.

Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.

Peak, M.J. et al. (1986). "DNA-to-Protein Crosslinks and Backbone Breaks Caused by FAR-and NEAR-Ultraviolet and Visible Light Radiations in Mammalian Cells," in *Mechanism of DNA Damage and Repair, Implications for Carcinogenesis and Risk Assessment*, SIMIC, M.G. (ed.).et al., Plenum Press, 233 Spring Street, New York, N.Y. 10013, pp. 193-202.

Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract).

Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.

Perez, M.T. et al. (Sep. 2002). "In Vivo Studies on Mouse Erythrocytes Linked to Transferrin," *IUBMB Life* 54(3):115-121.

Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).

Phillips, R.P. et al. (1991). "Quantification of Diabetic Maculopathy by Digital Imaging of the Fundus," *Eye* 5(1):130-137.

Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.

Profio, A.E. et al. (Jul.-Aug. 1984). "Fluorometer for Endoscopic Diagnosis of Tumors," *Medical Physics* 11(4):516-520.

Profio, A.E. et al. (Jun. 1, 1991). "Endoscopic Fluorescence Detection of Early Lung Cancer," *Proc. SPIE* 1426:44-46.

Profio, A.E. et al. (Nov./Dec. 1979). "Laser Fluorescence Bronchoscope for Localization of Occult Lung Tumors," *Medical Physics* 6:523-525.

Profio, A.E. et al. (Sep.-Oct. 1986). "Digital Background Subtraction for Fluorescence Imaging," *Medical Physics* 13(5):717-721.

Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.

Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.

Raabe et al. (2009, e-published on Nov. 12, 2008). "Laser Doppler Imaging for Intraoperative Human Brain Mapping", *NeuroImage* 44:1284-1289.

Raabe, A. et al. (Jan. 2003). "Near-Infrared Indocyanine Green Video Angiography: A New Method for Intraoperative Assessment of Vascular Flow," *Neurosurgery* 52(1):132-139.

Rava, R.P. et al. (Jun. 1, 1991). "Early Detection of Dysplasia in Colon and Bladder Tissue Using Laser-Induced Fluorescence," *Proc. SPIE* 1426:68-78.

Razum, N. et al. (Nov. 1987). "Skin Photosensitivity: Duration and Intensity Following Intravenous Hematoporphyrin Derivatives, HpD and DHE, " *Photochemistry and Photobiology* 46(5):925-928.

Report on Observation by C2400-75i and ARGUS20 Under Low illumination conditions, Jan. 17, 2008.

Request for invalidation of Japanese Patent JP3881550 filed by Hamamatsu Photonics, Inc (with English Translation).

Reuthebuch, O et al. (Feb. 2004). "Novadaq SPY: Intraoperative Quality Assessment in Off Pump Coronary Artery Bypass Grafting," *Chest* 125(2):418-424.

Reuthebuch, O.T. et al. (May 2003). "Graft Occlusion After Deployment of the Symmetry Bypass System," *Ann. Thorac. Surg.* 75(5):1626-1629.

Richards-Kortum, R. et al. (Jun. 1991). "Spectroscopic Diagnosis of Colonic Dysplasia: Spectroscopic Analysis," *Biochemistry and Photobiology* 53(6):777-786.

Roberts, W.W. et al. (Dec. 1997). "Laparoscopic Infrared Imaging," *Surg. Endoscopy* 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.

Ropars, C. (ed.) et al. (1987). *Red Blood Cells as Carriers for Drugs. Potential therapeutic Applications*, Pergamon Press, Oxford, New York, pp. v-vii, (Table of Contents only).

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.

Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.

Rossi, L. et al. (2001). "Erthrocyte-Mediated Delivery of Dexamethasone in Patients with Chronic Obstructive Pulmonary Disease," *Biotechnol. Appl. Biochem.* 33:85-89.

Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.

Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

Rozen, W.M. et al. (Jan. 2008). "Preoperative Imaging for DIEA Perforator Flaps: a Comparative Study of Computed Tomographic Angiography and Doppler Ultrasound," *Plastic and Reconstructive Surgery* 121(1):9-16.

Rubben, A. et al. (Mar. 1994). "Infrared Videoangiofluorography of the Skin with Indocyanine Green—Rat Random Cutaneous Flap Model and Results in Man," *Microvascular Research* 47(2):240-251.

(56) References Cited

OTHER PUBLICATIONS

Rubens, F.D. et al. (2002). "A New and Simplified Method for Coronary and Graft Imaging During CABG," *The Heart Surgery Forum* 5(2):141-144.

Sakatani, K. et al. (Nov. 1997). "Noninvasive Optical Imaging of the Subarchnoid Space and Cerebrospinal Fluid Pathways Based on Near Infrared Fluorescence," *J. Neurosurg.* 87(5) :738-745.

Salmon, E.D. et al. (Oct. 1994). "High Resolution Multimode Digital Imaging System for Mitosis Studies In Vivo and In Vitro," *Biol. Bull* 187(2):231-232.

Sato, et al., (1991). "Development of a Visualization Method for the Microcirculation of Deep Viscera Using an Infrared Intravital Microscope System," *Research on ME Devices and ME Technology* (with English Translation), five pages.

Satpathy G.R. et al. (Oct. 2004) "Loading Red Blood Cells with Trehalose: A Step Towards Biostabilization," *Cryobiology* 49(2):123-136.

Schaff, H.V. et al. (Oct. 15, 1996). "Minimal Thoracotomy for Coronary Artery Bypass: Value of Immediate Postprocedure Graft Angiography," *Supplement to Circulation* 94(8):1-51, (Abstract No. 0289), two pages.

Schellingerhout, D. et al. (Oct. 2000). "Quantitation of HSV Mass Distribution in a Rodent Brain Tumor Model," *Gene Therapy* 7(19):1648-1655.

Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.

Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.

Schneider Jr., H.C. et al. (Jan. 1975). "Fluorescence of Testicle, An Indication of Viability of Spermatic Cord After Torsion," *Urology* V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.

Sekijima, M. et al. (Sep. 2004). "An Intraoperative Fluorescent Imaging System in Organ Transplantation," *Transplantation Proceedings* 36(7):2188-2190.

Serov, A. et al. (Mar. 1, 2002). "Laser Doppler Perfusion Imaging with a Complimentary Metal Oxide Semiconductor Image Sensor," *Optics Letters* 27(5):300-302.

Serov, A.N. et al. (Sep. 23, 2003). "Quasi-Parallel Laser Doppler Perfusion Imaging Using a CMOS Image Sensor," *Proc. SPIE* 5067:73-84.

Sherif, A. et al. (Sep. 2001). "Lymphatic Mapping and Detection of Sentinel Nodes in Patients with Bladder Cancer," *The Journal of Urology* 166(3):812-815.

Sheth, S.A. et al. (Apr. 22, 2004)"Linear and Nonlinear Relationships between Neuronal Activity, Oxygen Metabolism, and Hemodynamic Responses," *Neuron* 42(2):347-355.

Shoaib, T. et al. (Jun. 1, 2001). "The Accuracy of Head and Neck Carcinoma Sentinel Lymph Node Biopsy in the Clinically NO Neck," *Cancer* 91(11):2077-2083.

Siemers, B.M. et al. (Nov. 2001). "The Acoustic Advantage of Hunting at Low Heights Above Water: Behavioual Experiments on the European 'Trawling' Bats Myotis Capaccinii, M Dasycneme and M. Daubentonii," *J. Eperimental Biol.* 204(Pt. 22):3843-3854.

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

Soltesz, E.G. et al. (Jan. 2005). "Intraoperative Sentine Lymph Node Mapping of the Lung Using Near-Infrared Fluorescent Quantum Dots," *Ann. Thorac. Surg.* 79(1):269-277.

Staurenghi, G. et al. (Dec. 2001)."Combining Photodynamic Therapy and Feeder Vessel Photocoagulation: A Pilot Study," *Seminars in Ophthalmology* 16(4):233-236.

Stern, M.D. (Mar. 6, 1975). "In Vivo Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Taggart, D.P. et al. (Mar. 2003). "Preliminary Experiences with a Novel lntraoperative Fluorescence Imaging Technique to Evaluate the Patency of Bypass Grafts in Total Arterial Revascularization," *Ann Thorac Surg.* 75(3):870-873.

Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor, K.M. (Apr. 1998). "Brain Damage During Cardiopulmonary Bypass," *Annals of Thoracic Surgery* 65(4):S20-S26.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.

Torok, B. et al. (May 1996). "Simultaneous Digital Indocyanine Green and Fluorescein Angiography," *Klinische Monatsblatter Fur Augenheilkunde* 208(5):333-336.

Tsutsumi, D. et al. "Moisture Detection of road surface using infrared camera," Reports of the Hokkaido Industrial Research Institute (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.

(56) References Cited

OTHER PUBLICATIONS

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ϵ-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

Wachi, A. et al. (Apr. 1995). "Characteristics of Cerebrospinal Fluid Circulation in Infants as Detected With MR Velocity Imaging," *Child's Nerv System* 11(4):227-230.

Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.

Weinbeer, M. et al. (Nov. 25, 2013). "Behavioral Flexibility of the Trawling Long-Legged Bat, Macrophyllum Macrophyllum (Phyllostomidae)," *Frontiers in Physiology* 4(Article 342):1-11.

What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj> last visited on Jan. 7, 2016, two pages.

Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.

Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.

Wollert, H.G. et al. (Dec. 1989). "Intraoperative Visualization of Coronary Artery Fistula Using Medical Dye," *The Thoracic and Cardiovascular Surg.* 46(6):382-383.

Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.

Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.

Yoneya, S. et al. (Jun. 1998). "Binding Properties of Indocyanine Green in Human Blood," *IOVS* 39(7):1286-1290.

Yoneya, S. et al. (Sep. 1993). "Improved Visualization of the Choroidal Circulation with Indocyanine Green Angiography," *Arch Opthalmol.* 111(9):1165-1166.

Young. I.T. et al. (1993). "Depth of Focus in Microscopy," SCIA '93, Proc. of the 8th Scandinavian Conference on Image Analysis, Tromso, Norway, pp. 493-498, six pages.

Canadian Office Action dated Mar. 16, 2016, for CA Application No. 2,750,760 filed on Jan. 23, 2009, five pages.

Canadian Office Action dated Sep. 30, 2015, for CA Application No. 2,811,847, filed on Sep. 20, 2011, four pages.

Chinese Third Office Action dated Aug. 8, 2016 for Chinese Application No. 201180057244.8, filed on Sep. 20, 2011, eighteen pages.

EP Communication in pursuant to Article 94(3) EPC dated Mar. 9, 2016 for European Patent Application No. 09739980.2 filed May 1, 2009, five pages.

European Communication pursuant to Article 94(3) dated May 27, 2016 for EP Application No. 15160177.0 filed on Aug. 11, 2000, five pages.

European Decision in Opposition Proceeding Revoking (Jun. 10, 2010). European Patent No. 1 143 852, thirty pages.

European Opposition of European Patent No. EP1143852 lodged by Hamamatsu Photonics, Inc., Jul. 30, 2008.

European Summons to attend Oral Proceedings pursuant to Rule 115(1) EPC issued on Apr. 25, 2016, for European patent application No. 09732993.2, filed on Apr. 14, 2009, five pages.

Extended European Search Report dated Oct. 14, 2015 for EP Application No. 13806313.6 filed on Jun. 20, 2013, nine pages.

Final Office Action dated Apr. 10, 2008, for U.S. Appl. No. 11/106,154, filed Apr. 14, 2005, six pages.

Final Office Action dated Apr. 2, 2013, for U.S. Appl. No. 13/419,368, filed Mar. 13, 2012, five pages.

Final Office Action dated Apr. 20, 2016, for U.S. Appl. No. 14/543,429, filed Nov. 17, 2014, seven pages.

Final Office Action dated Apr. 27, 2011 for U.S. Appl. No. 11/515,419, filed Sep. 1, 2006, nine pages.

Final Office Action dated Aug. 10, 2012, for U.S. Appl. No. 11/912,877, filed Aug. 13, 2008, ten pages.

Final Office Action dated Dec. 31, 2015 for U.S. Appl. No. 14/177,050 filed Feb. 10, 2014, eighteen pages.

Final Office Action dated Dec. 4, 2014, for U.S. Appl. No. 12/776,835, filed May 10, 2010, thirteen pages.

Final Office Action dated Feb. 1, 2013, for U.S. Appl. No. 12/776,835, filed May 10, 2010, thirteen pages.

Final Office Action dated Feb. 13, 2015, for U.S. Appl. No. 14/543,429, filed Nov. 17, 2014, six pages.

Final Office Action dated Feb. 18, 2010, for U.S. Appl. No. 11/106,154, filed Apr. 14, 2005, six pages.

Final Office Action dated Feb. 4, 2015 for U.S. Appl. No. 13/314,418, filed Dec. 8, 2011, six pages.

Final Office Action dated Jul. 21, 2016 for U.S. Appl. No. 14/543,356, filed Nov. 17, 2014, seven pages.

Final Office Action dated Jul. 9, 2015, for U.S. Appl. No. 14/543,356, filed Nov. 17, 2014, eight pages.

Final Office Action dated Jun. 1, 2015, for U.S. Appl. No. 14/543,429, filed Nov. 17, 2014, nine pages.

Final Office Action dated Jun. 13, 2014, for U.S. Appl. No. 12/776,835, filed May 10, 2010, thirteen pages.

Final Office Action dated Mar. 28, 2013 for U.S. Appl. No. 12/063,349, filed May 12, 2010, twenty pages.

Final Office Action dated Nov. 6, 2013, for U.S. Appl. No. 13/419,368, filed Mar. 13, 2012, five pages.

Final Office Action dated Oct. 7, 2011 for U.S. Appl. No. 11/851,312, filed Sep. 6, 2007, ten pages.

Final Office Action dated Sep. 13, 2011, for U.S. Appl. No. 11/106,154, filed Apr. 14, 2005, five pages.

Final Office Action dated Sep. 17, 2014 for U.S. Appl. No. 11/515,419, filed Sep. 1, 2006, eleven pages.

Final Office Action dated Sep. 23, 2004, for U.S. Appl. No. 09/744,034, filed Apr. 27, 2001, seven pages.

Final Office Action dated Sep. 29, 2016, for U.S. Appl. No. 13/922,996, filed Jun. 20, 2013, fourteen pages.

Indian Examination Report dated Sep. 22, 2016 for Indian Application No. 7566/DELNP/2010, filed on Oct. 27, 2010, nine pages.

International Preliminary Examination Report completed on Jul. 1, 2001 for PCT/US00/22088, filed on Aug. 11, 2000, three pages.

International Search Report and Written Opinion dated Jul. 29, 2009 for PCT/US2009/043975 filed on May 14, 2009, eleven pages.

International Search Report for Application No. PCT/EP2008/008547, dated Jun. 2, 2009; six pages.

International Search Report dated Dec. 3, 2015 for PCT Application No. PCT/CA2015/050973 filed on Sep. 28, 2015, three pages.

International Search Report dated Jan. 22, 2014, for PCT Application No. PCT/IB2013/001934, filed on Jun. 20, 2013, four pages.

International Search Report dated Oct. 18, 2000, for PCT Application No. PCT/US2000/22088, filed on Aug. 11, 2000, one page.

International Search Report dated Sep. 11, 2009 for Application No. PCT/US2009/042606 filed on May 1, 2009, five pages.

Japanese First Office Action dated Feb. 1, 2016 for Japanese Patent Application No. 2015-517876 filed Jun. 20, 2013, eight pages.

Japanese Notice of Allowance dated Sep. 16, 2016, for Japanese Patient Application No. 2015-517876 filed on Jun. 20, 2013, six pages.

Japanese Office Action dated Apr. 1, 2016, for Japanese Patent Application No. 2013-529729, filed on Mar. 21, 2013, and an English translation of the same, seven pages.

(56) References Cited

OTHER PUBLICATIONS

Korean Notice of Allowance dated Apr. 29, 2016, for Korean Patent Application No. 10-2010-7024977, filed on Apr. 14, 2009, and an English translation of the same, three pages.
Korean Patent Office, Office Action dated Jun. 25, 2014 in Korean Patent Application No. 10-2013-7035027 w/English-language Translation, fifteen pages.
Non-Final Office Action dated Apr. 26, 2012, for U.S. Appl. No. 12/776,835, filed May 10, 2010, nine pages.
Non-Final Office Action dated Apr. 28, 2010, for U.S. Appl. No. 11/946,672, filed Nov. 28, 2007, nine pages.
Non-Final Office Action dated Aug. 10, 2016 for U.S. Appl. No. 14/177,050, filed Feb. 10, 2014, twenty pages.
Non-Final Office Action dated Aug. 29, 2014 for U.S. Appl. No. 12/063,349, filed May 12, 2010, nineteen pages.
Non-Final Office Action dated Dec. 30, 2010, for U.S. Appl. No. 11/106,154, filed Apr. 14, 2005, six pages.
Non-Final Office Action dated Feb. 1, 2011 for U.S. Appl. No. 11/851,312, filed Sep. 6, 2007, seven pages.
Non-Final Office Action dated Feb. 5, 2016, for U.S. Appl. No. 14/543,356, filed Nov. 17, 2014, seven pages.
Non-Final Office Action dated Jan. 22, 2014 for U.S. Appl. No. 11/851,312, filed Sep. 6, 2007, ten pages.
Non-Final Office Action dated Jan. 27, 2012, for U.S. Appl. No. 11/912,877, filed Aug. 13, 2008, eleven pages.
Non-Final Office Action dated Jan. 9, 2009, for U.S. Appl. No. 11/106,154, filed Apr. 14, 2005, six pages.
Non-Final Office Action dated Jul. 2, 2015, for U.S. Appl. No. 14/177,050, filed Feb. 10, 2014, nineteen pages.
Non-Final Office Action dated Jul. 22, 2015 for U.S. Appl. No. 13/314,418, filed Dec. 8, 2011, six pages.
Non-Final Office Action dated Jul. 8, 2014 for U.S. Appl. No. 13/314,418, filed Dec. 8, 2011, seven pages.
Non-Final Office Action dated Jun. 11, 2013 for U.S. Appl. No. 11/515,419, filed Sep. 1, 2006, eleven pages.
Non-Final Office Action dated Jun. 28, 2012 for U.S. Appl. No. 12/063,349, filed May 12, 2010, seventeen pages.
Non-Final Office Action dated Mar. 10, 2004, for U.S. Appl. No. 09/744,034, filed Apr. 27, 2001, seven pages.
Non-Final Office Action dated Mar. 13, 2015, for U.S. Appl. No. 14/543,356, filed Nov. 17, 2014, eight pages.
Non-Final Office Action dated Mar. 6, 2007, for U.S. Appl. No. 11/106,154, filed Apr. 14, 2005, eight pages.
Non-Final Office Action dated May 21, 2015, for U.S. Appl. No. 13/922,996, filed Jun. 20, 2013, fourteen pages.
Non-Final Office Action dated May 6, 2015 for U.S. Appl. No. 12/063,349, filed May 12, 2010, seventeen pages.
Non-Final Office Action dated Nov. 27, 2015, for U.S. Appl. No. 14/543,429, filed Nov. 17, 2014, six pages.
Non-Final Office Action dated Nov. 9, 2015, for U.S. Appl. No. 14/177,045, filed Feb. 10, 2014, seven pages.
Non-Final Office Action dated Oct. 3, 2013, for U.S. Appl. No. 12/776,835, filed May 10, 2010, twelve pages.
Non-Final Office Action dated Sep. 15, 2010, for U.S. Appl. No. 11/106,154, filed Apr. 14, 2005, six pages.
Non-Final Office Action dated Sep. 30, 2010 for U.S. Appl. No. 11/515,419, filed Sep. 1, 2006, eleven pages.
Non-Final Office Action dated Sep. 5, 2012, for U.S. Appl. No. 12/933,477, filed Sep. 20, 2010, seven pages.
Notice of Allowance dated Jul. 13, 2016 for U.S. Appl. No. 14/598,832, filed Jan. 16, 2015, seven pages.
Notice of Allowance dated Apr. 17, 2014, for U.S. Appl. No. 13/419,368, filed Mar. 13, 2012, five pages.
Notice of Allowance dated Mar. 15, 2016, for U.S. Appl. No. 14/598,832, filed Jan. 16, 2015, seven pages.
Notice of Allowance dated Mar. 7, 2005, for U.S. Appl. No. 09/744,034, filed Apr. 27, 2001, five pages.
Notice of Allowance dated May 26, 2016, for U.S. Appl. No. 14/177,045, filed Feb. 10, 2014, eight pages.
Notice of Allowance dated Nov. 30, 2010, for U.S. Appl. No. 11/946,672, filed Nov. 28, 2007, six pages.
Notice of Allowance dated Oct. 4, 2013, for U.S. Appl. No. 11/912,877, filed Aug. 13, 2008, nine pages.
Notice of Allowance dated Oct. 6, 2014, for U.S. Appl. No. 13/419,368, filed Mar. 13, 2012, five pages.
Notification of Transmittal of International Search Report and the Written Opinion of the International Searching Authority, or the Declaration dated Apr. 3, 2008 for PCT/US07/77892, filed on Sep. 7, 2007, ten pages.
Partial European Search Report dated Dec. 16, 2010 for European Application No. 10186218.3 filed on Aug. 11, 2000, seven pages.
Partial European Search Report dated Jun. 11, 2014 for European Application No. 13178642.8, filed on May 1, 2009, five pages.
Supplemental European Search Report for EP Application No. 00955472.6 dated Jul. 6, 2004, five pages.
Written Opinion for Application No. PCT/EP2008/008547, dated Jun. 2, 2009; eleven pages.
Written Opinion of the International Searching Authority dated Jan. 22, 2014, for PCT Application No. PCT/IB2013/001934, filed on Jun. 20, 2013, six pages.
Canadian Office Action dated Jan. 19, 2017 for Canadian Application No. 2,914,778 filed on Dec. 8, 2015, four pages.
Canadian Office Action dated Oct. 25, 2016 for Canadian Patent Application No. 2,811,847, filed on Sep. 20, 2011, three pages.
European Communication pursuant to Rules 70(2) and 70a(2) EPC in EP Application No. 16163909.1, dated Nov. 14, 2016, two pages.
European Summons to attend Oral Proceedings pursuant to Rule 115(1) EPC dated Dec. 16, 2016, for European patent application No. 15160177.0, filed on Aug. 11, 2000, seven pages.
International Search report dated Jul. 4, 2008 for International Application No. PCT/US2007/080847, filed on Oct. 9, 2007, three pages.
U.S. Non-Final Office Action dated Dec. 16, 2016, for U.S. Appl. No. 14/868,369, filed Sep. 28, 2015, seven pages.
U.S. Non-Final Office Action dated Oct. 12, 2016, for U.S. Appl. No. 14/543,429, filed Nov. 17, 2014, nine pages.
U.S. Non-Final Office Action dated Oct. 28, 2016, for U.S. Appl. No. 14/543,356, filed Nov. 17, 2014, eight pages.
U.S. Notice of Allowance dated Dec. 2, 2016, for U.S. Appl. No. 14/598,832, filed Jan. 16, 2015, seven pages.
Written Opinion of the International Searching Authority dated Jul. 4, 2008 for International Application No. PCT/US2007/080847, filed on Oct. 9, 2007, six pages.
Declaration of Brian Wilson dated Aug. 22, 2017 for Inter Partes Review No. IPR2017-01426, twelve pages, [Exhibit 2002].
Definition of "Expose," Excerpt of Merriam Webster's Medical Desk Dictionary (1993), four pages, [Exhibit 2004].
Definition of "Graft," Excerpt of Stedman's Medical Dictionary for the Health Professions and Nursing; 6th Ed. (2008), three pages, [Exhibit 2003].
Enquist, L.W. et al. (2002). "Directional Spread of an α-Herpesvirus in the Nervous System," *Veterinary Microbiology* 86:5-16.
Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.
Hyvärinen, L. et al. (1980). "Indocyanine Green Fluorescence Angiography." *Acta ophthalmologica* 58(4):528-538. [Exhibit 1014].
Little, J.R. et al. (May 1979). "Superficial Temporal Artery to Middle Cerebral Artery Anastomosis: Intraoperative Evaluation by Fluorescein Angiography and Xenon-133 Clearance," *Journal of Neurosurgery* 50(5):560-569. [Exhibit 1002].
Magnani, M. et al. (1998). "Erythrocyte Engineering for Drug Delivery and Targeting," *Biotechnol. Appl. Biochem.* 28:1-6.
Novadaq Technologies Inc. (Jan. 19, 2005). 510(k) Summary—Showing X-Ray Fluoroscopy as Predicate Device, Fluorescent Angiographic System, six pages, [Exhibit 1012].
Sony Corporation. The Sony U-Matic Videocassette Recorder, VO-9800, ten pages, [Exhibit 1015].
Summary of Invention Submitted to EPO, "Development of Novadaq SPY™ Cardiac Imaging Invention," five pages, Exhibit 1011].

(56) References Cited

OTHER PUBLICATIONS

Canadian Notice of Allowance dated Jan. 4, 2018, for Canadian Application No. 2,750,760, filed on Jul. 25, 2008, one page.
Canadian Notice of Allowance dated Sep. 27, 2017, for Canadian Application No. 2,811,847, filed on Mar. 20, 2013, one page.
Canadian Office Action dated Feb. 27, 2017 for Canadian Application No. 2,750,760, filed on Jul. 25, 2011, three pages.
Canadian Office Action dated Feb. 13, 2018, for CA Application No. 2,963,450 filed on Apr. 3, 2017, three pages.
Canadian Office Action dated Feb. 28, 2018, for CA Application No. 2,963,987 filed on Mar. 27, 2017, five pages.
Canadian Office Action dated Nov. 28, 2017 for Canadian Application No. 2,914,778 filed on Dec. 8, 2015, six pages.
Chinese Fifth Office Action dated Dec. 19, 2017 for Chinese Application No. 201180057244.8 filed on Sep. 20, 2011, eleven pages.
Chinese First Office Action dated Apr. 6, 2017 for Chinese Application No. 201510214021.8, filed on May 14, 2009, fifteen pages.
Chinese Fourth Office Action dated Mar. 13, 2017 for Chinese Application No. 201180057244.8 filed on Sep. 20, 2011, twenty pages.
Chinese Second Office Action dated Feb. 8, 2018 for Chinese Application No. 201510214021.8, filed on May 14, 2009, seventeen pages.
European Communication Pursuant to Article 94(3) EPC dated Aug. 31, 2017, for EP Application No. 09739980.2 filed on Nov. 30, 2010, four pages.
European Communication Pursuant to Article 94(3) dated Sep. 21, 2017, for European Application No. 16163909.1 filed on Apr. 5, 2016, three pages.
European Communication Under Rule 71(3) EPC (Intention to Grant) dated Dec. 1, 2017, for European patent Application No. 09739980.2, filed on Nov. 30, 2010, seven pages.
European Communication under Rule 71(3) EPC (Intention to Grant) dated Nov. 21, 2017, for European Patent Application No. 15160177.0, filed on Aug. 11, 2000, seven pages.
European Decision of European Patent Office Technical Board of Appeal Revoking Counterpart Patent No. 1143852, dated Oct. 23, 2013. [Exhibit-1009].
European Decision to Grant dated Apr. 21, 2017 for EP Application No. 09732993.2, filed on Nov. 8, 2010, two pages.
Extended European Search report dated Sep. 16, 2016 for EP Application No. 16183434.6 filed on Aug. 9, 2016, ten pages.
Indian Examination Report dated Jan. 16, 2018 for Indian Application No. 2993/DELNP/2011, filed on Apr. 25, 2011, eleven pages.
Indian Examination Report dated Jul. 28, 2017 for Indian Application No. 1983/MUMNP/2007, filed on Nov. 27, 2007, seven pages.
International Preliminary Report on Patentability dated Apr. 4, 2017, for PCT Application No. PCT/CA2015/050973 filed on Sep. 28, 2015, six pages.
International Search Report and Written Opinion dated Oct. 24, 2017 for PCT Application No. PCT/CA2017/050564 filed on May 10, 2017, fourteen pages.
Invitation to Pay Additional Fees and, Where Applicable, Protest Fee dated Jul. 4, 2017, for PCT/CA2017/050564, filed on May 10, 2017, two pages.

Japanese Final Office Action dated Feb. 5, 2018 for Japanese Patent Application No. 2016-014503, filed on Jan. 28, 2016, six pages.
Japanese First Office Action dated Jul. 28, 2017 for Japanese Patent Application No. 2016-203798 filed Oct. 17, 2016, four pages, (with English Translation).
Japanese Notice of Allowance dated Sep. 25, 2017 for Japanese Patent Application No. 2013-529729, filed on Mar. 21, 2013, six pages.
Japanese Office Action dated Mar. 3, 2017, for Japanese Patent Application No. 2016014503, filed on Jan. 28, 2016, ten pages.
Japanese Office Action dated Mar. 31, 2017 for Japanese Patent Application No. 2013-529729, filed on Mar. 21, 2013, eleven pages.
Japanese Office Action dated Mar. 19, 2018 for Japanese Application No. 2017-518785 filed on Apr. 7, 2017, eight pages.
Korean Notice of Allowance dated Apr. 27, 2017, for Korean Patent Application No. 10-2016-7007994, filed on Mar. 25, 2016, three pages.
Novadaq Technologies Inc.'s Preliminary Response filed on Aug. 23, 2017 to Petition for Inter Partes Review of U.S. Pat. No. 8,892, sixty one pages.
Partial European Search Report dated Jun. 28, 2016 for European Application No. 16163909.1 filed on Apr. 5, 2016, six pages.
Petition for Inter Partes Review of U.S. Pat. No. 8,892, (May 11, 2017), filed by Visionsense Corp., fifty four pages.
Translation of Decision of Japanese Patent Office Trial Board revoking Counterpart Patent No. U.S. Pat. No. 3,881,550, twenty six pages, [Exhibit 1010].
U.S. Final Office Action dated Apr. 12, 2017, for U.S. Appl. No. 14/543,429, filed Nov. 17, 2014, nine pages.
U.S. Final Office Action dated Mar. 20, 2017, for U.S. Appl. No. 14/177,050, filed Feb. 10, 2014, twenty three pages.
U.S. Non-Final Office Action dated Jan. 8, 2018, for U.S. Appl. No. 15/077,677, filed Mar. 22, 2016, nine pages.
U.S. Non-Final Office Action dated Jan. 31, 2018 for U.S. Appl. No. 15/799,727 filed Oct. 31, 2017, seven pages.
U.S. Non-Final Office Action U.S. Appl. No. Mar. 22, 2018 for U.S. Appl. No. 15/610,102, filed May 31, 2017, eleven pages.
U.S. Non-Final Office Action dated Oct. 13, 2017, for U.S. Appl. No. 13/922,996, filed Jun. 20, 2013, seventeen pages.
U.S. Non-Final Office Action dated Oct. 26, 2017, for U.S. Appl. No. 14/543,429, filed Nov. 17, 2014, nine pages.
U.S. Non-Final Office Action dated Sep. 27, 2017 for U.S. Appl. No. 14/177,050, filed Feb. 10, 2014, twenty two pages.
U.S. Notice of Allowance dated Dec. 6, 2017, for U.S. Appl. No. 15/476,290, filed Mar. 31, 2017, nine pages.
U.S. Notice of Allowance dated Jul. 12, 2017, for U.S. Appl. No. 14/868,369, filed Sep. 28, 2015, nine pages.
U.S. Notice of Allowance dated Mar. 29, 2018, for U.S. Appl. No. 14/177,050, filed Feb. 10, 2014, ten pages.
U.S. Restriction Requirement dated Jun. 26, 2017, for U.S. Appl. No. 15/077,677, filed Mar. 22, 2016, seven pages.
Written Opinion of the International Searching Authority dated Dec. 3, 2015 for PCT Application No. PCT/CA2015/050973 filed on Sep. 28, 2015, five pages.
U.S. Appl. No. 15/591,909, filed May 10, 2017, by Moore et al. (Copy not submitted herewith pursuant to the waiver of 37 C.F.R. § 1.98(a)(2)(iii) issued by the Office on Sep. 21, 2004.).

* cited by examiner

LOCATING AND ANALYZING PERFORATOR FLAPS FOR PLASTIC AND RECONSTRUCTIVE SURGERY

CROSS-REFERENCE TO RELATED APPLICATIONS

This application is a continuation-in-part of prior filed copending PCT International application no. PCT/IB2009/05700, filed Apr. 14, 2009, which designated the United States and has been published as International Publication No. WO/2009/127972 in the English language, and which claims the benefit of U.S. Provisional Application Ser. No. 61/044,779, filed Apr. 14, 2008.

This application also claims the benefit of prior filed U.S. provisional Application No. 61/243,688, filed Sep. 18, 2009, the entire contents of which are incorporated herein by reference.

BACKGROUND OF THE INVENTION

Plastic and reconstructive surgery often entails the localization and clinical evaluation of a flap of skin and subcutaneous tissue which is supplied by isolated perforator vessels and that is potentially suitable for grafting in another part of the body. Perforators pass from their source vessel to the skin surface, either through or between deep muscular tissues. Well-vascularised flaps are good candidates for grafts.

For example, abdominal donor-site flaps have become the standard for autologous breast reconstruction since the early 1980s. Within the abdomen, free fat options range from complete transverse rectus abdominis musculocutaneous (TRAM) flaps to isolated perforator flaps, such as the deep inferior epigastric artery (DIEA) perforator flap. Perforator flaps have allowed the transfer of the patient's own skin and fat in a reliable manner also in other areas of tissue reconstruction, with minimal donor-site morbidity. Flaps that relied on a random pattern blood supply were soon supplanted by pedicled, axial patterned flaps that could reliably transfer great amounts of tissue. The advent of free tissue transfer allowed an even greater range of possibilities to appropriately match donor and recipient sites. The increased use of perforator flaps has escalated the need for a pre-operative familiarity of an individual's particular anatomical feature of the DIEA and its perforating branches, particularly given the significant variation in that anatomy of the vascular supply to the abdominal wall.

Localization and evaluation of perforators is a painstaking and time-consuming process. Pre-operative computed tomography angiographic (CTA) imaging is often performed to do the localization. Such an approach entails considerable expense and has the additional complication that the surgeon must mentally correlate the images from the previously acquired 3D modality with the current 2D view of the patient now lying on the operating table. The search for a more favorable imaging modality is thus continuing, with recent interest in the use of indocyanine green (ICG) fluorescence imaging, wherein blood circulation is assessed through the skin on the basis of a fluorescence signal. Fluorescence in ICG with an emission peak around 830 nm occurs as a result of excitation by radiation in the near-infrared spectral range. Excitation light with a wavelength around 800 nm can be produced, for example, by a diode laser, light emitting diodes (LED), or other conventional illumination sources, such as arc lamps, halogen lamps with a suitable bandpass filter. The skin is transparent to this wavelength.

ICG strongly binds to blood proteins and has previously been used for cardiac output measurement, hepatic function evaluation, and ophthalmic angiography, with few adverse reactions. Evaluation of ICG fluorescence signals can be used to locate perforators. Since the skin surface near a perforator generally accumulates more blood and at a faster rate than the surrounding tissue, once ICG is injected, perforators tend to fluoresce brighter and faster than the surrounding tissue. This rapid, high-intensity fluorescence enables visual localization of the perforator. Often, however, the surgeon is interested not merely in localization but also in evaluation and comparison to support good clinical decision making. The surgeon needs to decide which of several perforators the best graft candidates are. Here, simple visual observation while fluorescence rapidly accumulates and dissipates does not suffice. For example, the tendency of residual ICG from successive injections to accumulate in tissue and to gradually raise the background brightness with each injection further confounds easy visual discrimination of the best candidate perforators. In addition, ICG sometimes moves exceedingly slowly over several minutes making such on-the-fly analysis very challenging and subjective. A surgeon will make an assessment by raising the following questions:
1) How much ICG-bound blood is in the tissue?
2) How long does it stay in the tissue?
3) How quickly does it move through the tissue?
4) After the bolus is injected, in which order do anatomical areas light up?

These questions are difficult to answer on a subjective basis. Accordingly, there is a need for more advanced image processing and display methods to apply objective standards to localize and evaluate perforators.

SUMMARY OF THE INVENTION

According to one aspect of the invention, a method for preoperative identification of a perforator vessel for plastic and/or reconstructive surgery using ICG fluorescence angiography imaging is disclosed, which includes time-resolved image processing to highlight perforator locations and to enable visual discrimination among candidate perforators by various computed metrics. The surgeon is able to select and compare the results of algorithms that analyze the time series and output the metrics according to at least one of the following processing acts:
Determine time-integrated fluorescence on a pixel-by-pixel basis. Compute an average fluorescence by dividing the time-integrated fluorescence by the elapsed time.
Determine a rate of increase/wash-out in the fluorescence.
Determine the elapsed time to achieve peak fluorescence.

The various image processing steps process the image pixels independently and compute a unique numerical metric for each pixel in the input sequence observed across the entire time of the acquisition or a selected temporal sub-range. Each image output is thus a numerical array having the same dimensions, i.e. number and arrangement of pixels, as a frame in the input image sequence. Thus, the processed image can be displayed, for example, as a three-dimensional representation, for example a contour map, of the computed pixel values across the imaged area, or as a color-coded two-dimensional image or a relief map. Such image representations facilitate rapid comprehension of image features and comparison between regions on the images, in this case the location of the perforators under the skin.

These and other features and advantages of the present invention will become more readily appreciated from the detailed description of the invention that follows.

BRIEF DESCRIPTION OF THE DRAWINGS

The following Figures depict certain illustrative embodiments of the invention in which like reference numerals refer to like elements. These depicted embodiments are to be understood as illustrative of the invention and not as limiting in any way.

DETAILED DESCRIPTION

The invention is directed to preoperative determination of the location of perforator vessels in perforator flaps by a non-invasive method, before any incision is made.

Figure 1:
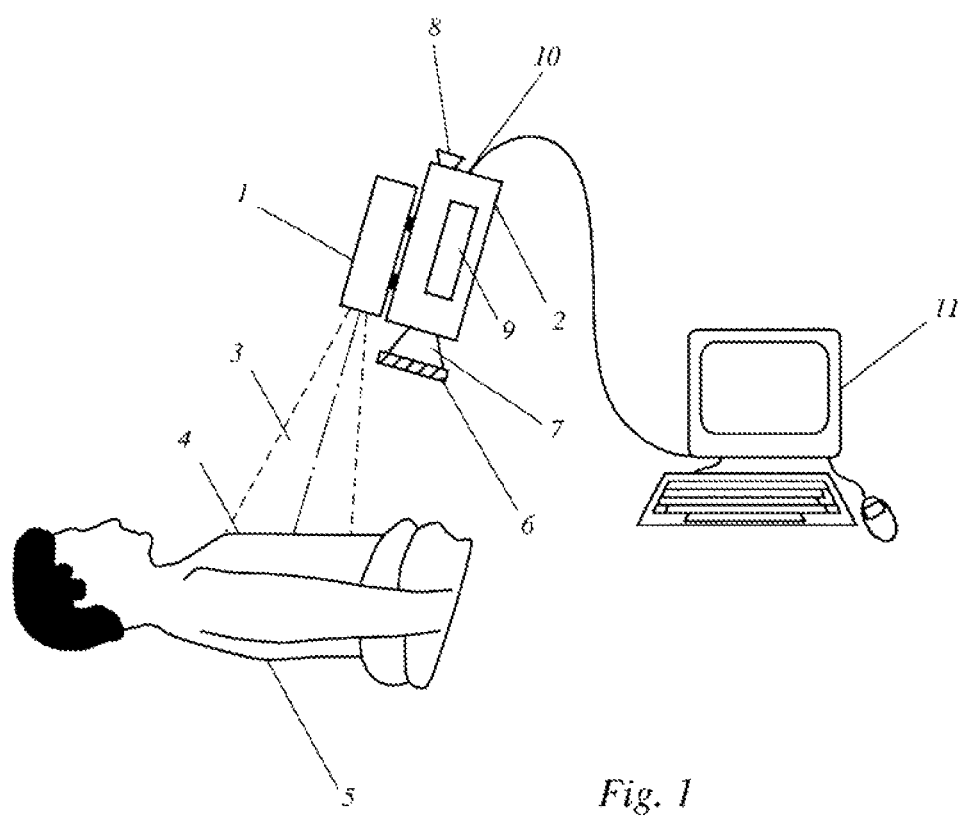
FIG. 1 shows schematically a camera system for observing ICG fluorescence.

FIG. 1 shows schematically a device for a non-invasive, through the skin determination of tissue perfusion in operative, in particular preoperative, applications by ICG fluorescence imaging. An infrared light source, for example, one or more diode lasers or LEDs, with a peak emission of about 780-800 nm for exciting fluorescence in ICG is located inside housing 1. The fluorescence signal is detected by a CCD camera 2 having adequate near-IR sensitivity; such cameras are commercially available from several vendors (Hitachi, Hamamatsu, etc.). The CCD camera 2 may have a viewfinder 8, but the image may also be viewed during the operation on an external monitor which may be part of an electronic image processing and evaluation system 11.

A light beam 3, which may be a divergent or a scanned beam, emerges from the housing 1 to illuminate an area of interest 4, i.e. the area where a flap with suitable perforator vessels is expected to be located. The area of interest may be about 10 cm×10 cm, but may vary based on surgical requirements and the available illumination intensity and camera sensitivity.

A filter 6 is typically placed in front of the camera lens 7 to block excitation light from reaching the camera sensor, while allowing fluorescence light to pass through. The filter 6 may be an NIR long-wave pass filter (cut filter), which is only transparent to wavelengths greater than about 815 nm, or preferably a bandpass filter transmitting at peak wavelengths of between 830 and 845 nm and having a full width at half maximum (FWHM) transmission window of between about 10 nm and 25 nm, i.e. outside the excitation wavelength band. The camera 2 may also be designed to acquire a color image of the area of interest to allow real-time correlation between the fluorescence image and the color image.

In the context of the present invention, the device illustrated in FIG. 1 is used to identify/locate perforator vessels prior to surgery—this will assist the surgeon in selecting the best flap or flap zone for use during the reconstruction.

In other post-operative applications, the device can be used to:

Validate anastomotic patency and arterial and venous flow—this can potentially improve outcomes to eliminate flap failure which can be a result of poor arterial flow and inadequate perfusion as well as poor venous return resulting in congestion.

Visualize and confirm complete tissue perfusion, as microvascular perfusion to the entire flap and native tissue is critical to flap survival.

With the invention, perforator locations are visualized by image processing and presentation techniques to enable easy and objective visual discrimination among candidate perforators. ICG is injected and the entire ICG fluorescence perfusion and wash-out cycle is captured by the imaging device. After image acquisition, the entire sequence or some temporal sub-range of the images is processed by an image processing algorithm, which may be selected by the surgeon.

Processed results of the fluorescence measurements may be visualized, for example, as false color images or as a contour map, to enable rapid visual evaluation according to the applied algorithm metric. For example, the fluorescence intensity for each pixel may be rendered as a spectral color varying from blue ("cool" spots or low fluorescence-intensity or rate) to red ("hot" spots or high fluorescence-intensity or rate). Other spectral associations are easily accommodated. The output may be presented as a semi-transparent overlay on the original anatomical images. This enables visual correlation of "hot" spots with the underlying anatomy. The meaning of "hot" spots varies with the algorithm employed, such as integrated intensity, weighted or unweighted, rate of increase or wash-out.

The user is given interactive control over the "hot" to "cool" color mapping and can vary it in real time to explore finer or coarser sub-ranges of the dynamic range of each algorithm's output metric. As the color window is widened, the hottest regions are highlighted first, followed by the cooler regions. This kind of adjustment can be made by changing the mapping of luminosity or contrast between the acquired pixels and the pixels in the displayed image. Such mapping functions may be included in standard imaging programs. This windowing process based on the currently employed metric aids in discriminating between perforators and enhances perception and improves understanding by the surgeon of the applied ICG dynamics.

The invention also supports the simultaneous display and evaluation of two sequences from two different locations on the patient's skin. This enables comparison of candidate flaps that are separated by a distance greater than the imaging system's field of view.

Figure 2:
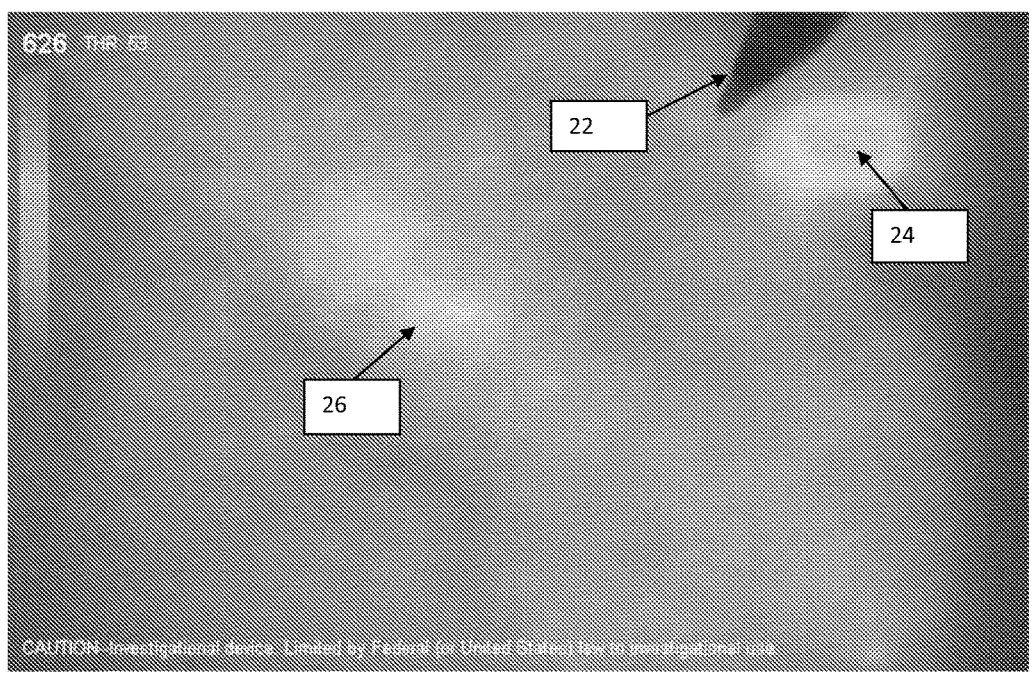
FIG. 2 shows an ICG fluorescence image of an area of skin, with the pixel values integrated over time.

FIG. 2 shows an image of an area of a patient's skin where suitable perforator vessels are to be identified. Each pixel represents the time integral of fluorescence intensity over the exposure time for the image sequence. This mode is typically referred to as "integration mode" in image processing and many image processors offer this mode as a standard feature. In practice, the pixel intensities (collected charges in a CCD) acquired during each frame in the image sequence are added on a pixel-by-pixel basis, for example in the image processor, and divided by the number of frames, whereafter the sum may be normalized to a fixed dynamic range, for example, from 1 to 255 (8-bits). The notion is that brighter pixels in an image represent an area of the skin infused with a greater volume of blood carrying ICG over a preset period of time. In FIG. 2, the perforator vessel 24 exhibits the highest integrated fluorescence intensity, with another perforator vessel exhibiting weaker fluorescence intensity shown as 26.

Note that the transparency of the image has been set such that the physician's marker 22 is visible through the transparent color overlay of the ICG fluorescence image at the upper right of the screen.

Figure 3:
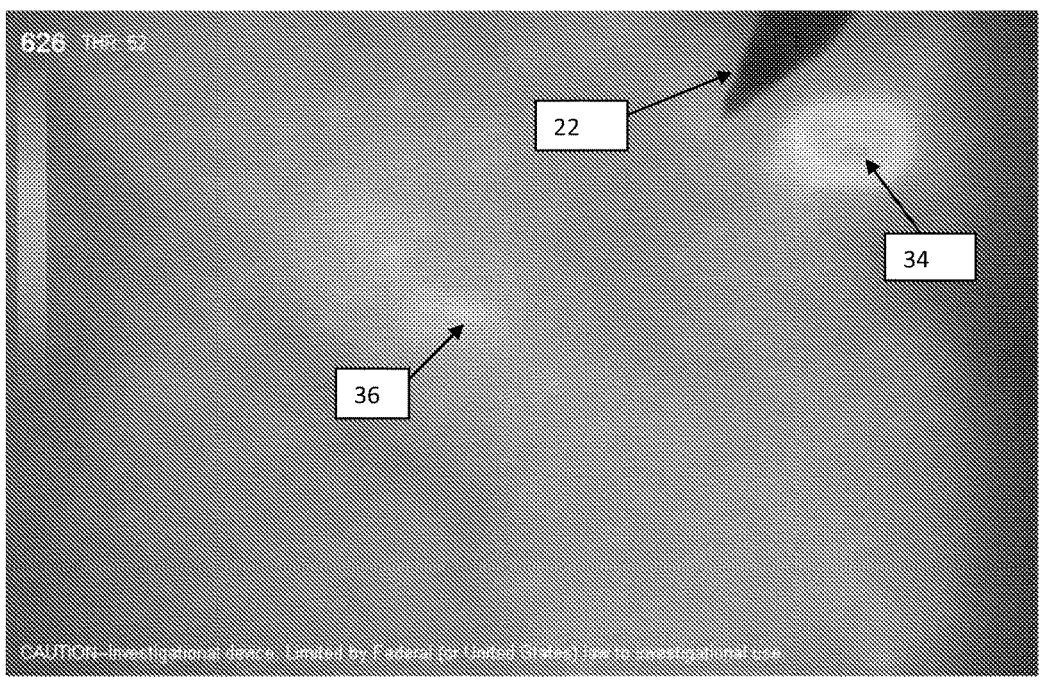
FIG. 3 shows an ICG fluorescence image of an area of skin integrated over time, with the pixel values inversely weighted by elapsed time.

FIG. 3 shows an ICG fluorescence image of the same area of skin integrated over time, with the pixel values inversely weighted by elapsed time. This image processing algorithm is similar to the previously described integration, but instead of adding the measured intensities of each pixel directly, the measured intensity values are first divided by the elapsed time after start of the observation of ICG fluorescence, before being added. In this way, earlier fluorescence signals are given a greater significance that fluorescence signals acquired later. The "hottest" pixels are those pixels that in the sequence of image frames fluoresce earlier than other pixels which the ICG bolus reaches at a later time. The same perforator vessel 34 is identified as in FIG. 2, with another vessel 36 barely identifiable.

Figure 4:
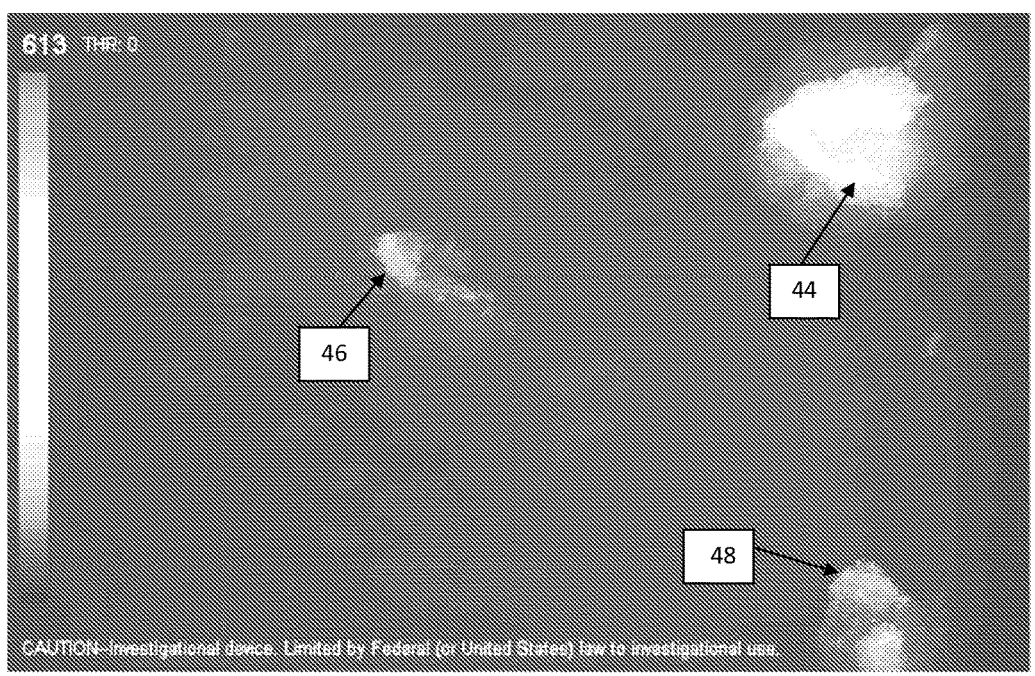
FIG. 4 shows an ICG fluorescence image of an area of skin, with the pixel values determined by the rate of increase of fluorescence.

FIG. 4 shows an ICG fluorescence image, again of the same area of skin, with the pixel values in this image determined by the rate of increase of fluorescence intensity. In this image processing algorithm, a slope of the pixel intensity versus elapsed time is computed for each pixel in an image. For example, each pixel may have an assigned lowest intensity value (baseline) and an assigned highest intensity value (or another relatively high-intensity value). For each pixel, the time when the pixel intensity crosses the baseline and the time when the pixel intensity crosses the high-intensity value are noted. From this information, the image processing algorithm computes a rate of increase for each pixel in the image, with "hotter" pixels having a greater slope, i.e., they reach the high-intensity value faster than "cooler" pixels. This embodiment of the image processing algorithm thus highlights the speed at which the ICG bolus reaches the perforator vessels. The transparency has been turned off in FIG. 4, so that the surgeon's tool is not visible in the image.

The previously identified perforator vessel, shown here with the reference symbol 44, is much better defined, as are the vessel 46 (previously shown as 26 and 36) and another vessel 48.

Figure 5:
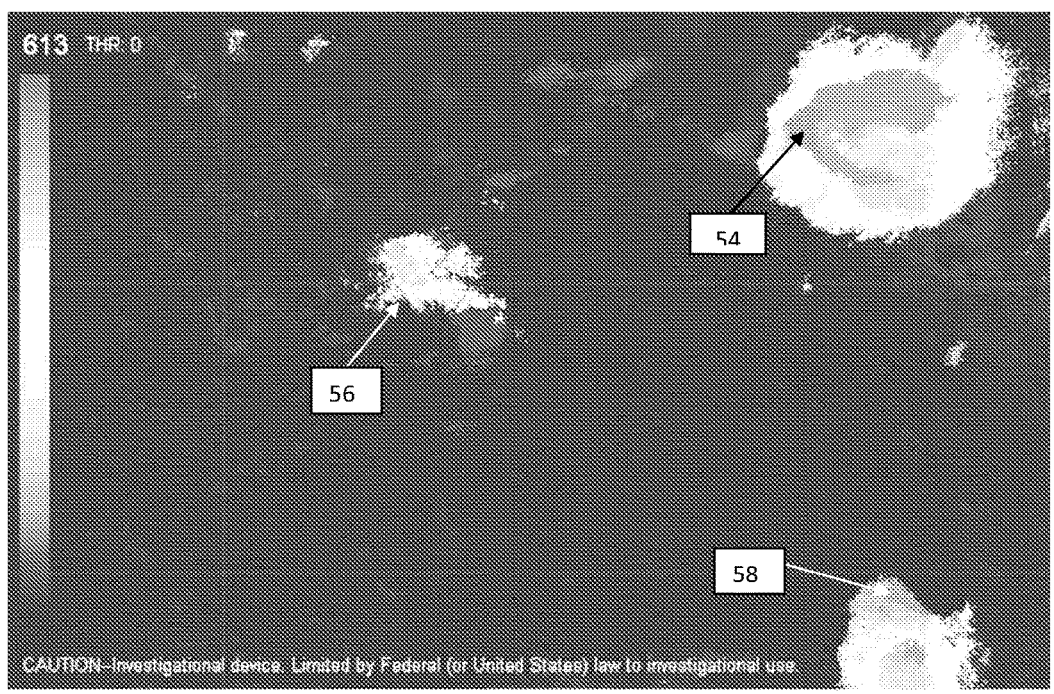
FIG. 5 shows an ICG fluorescence image of an area of skin, with the pixel values determined by elapsed time to maximum fluorescence.

FIG. 5 shows an ICG fluorescence image of the same area of skin, with the pixel values determined by elapsed time to maximum fluorescence. Unlike FIG. 4, which displays the time rate of change, the image processing algorithm of FIG. 5 displays the time at which pixels reach their maximum intensity, with the "hotter" pixels reaching their respective peak fluorescence intensity sooner than cooler pixels. The algorithm thus highlights areas of the image in the order in which perforators reach their peak intensity. In this image, the previously identified perforator vessels 24, 34, 44 is again clearly distinguishable, as are the vessels 56 and 58 which correspond to the vessels 46 and 48 of FIG. 4.

Figure 6:
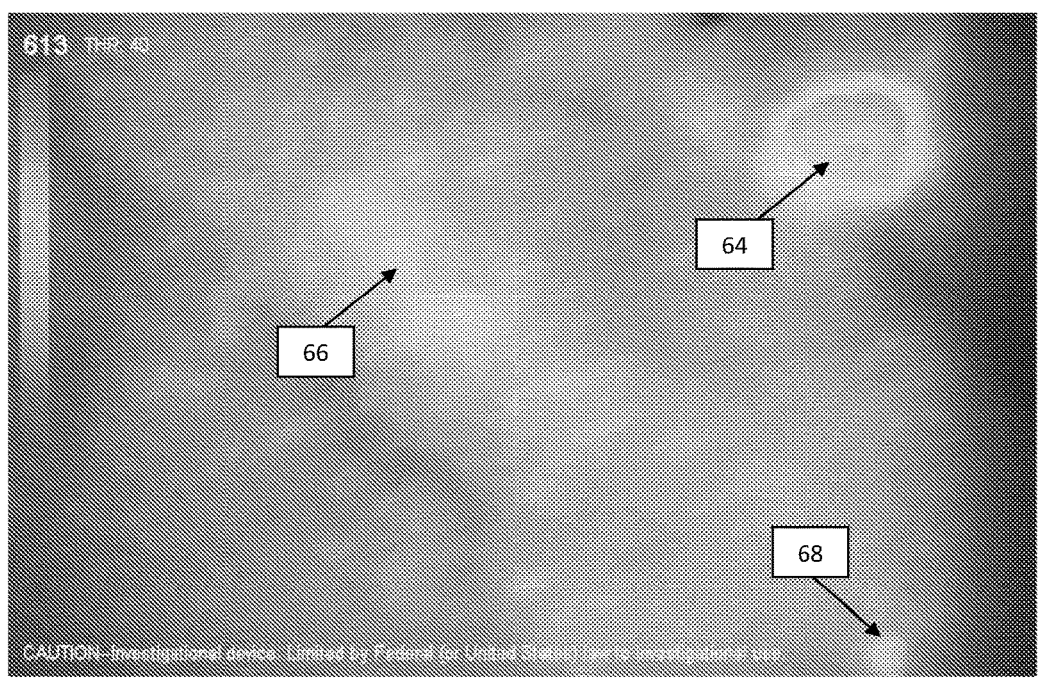
FIG. 6 shows an ICG fluorescence image of an area of skin, with the pixel values determined by peak fluorescence.

FIG. 6 shows an ICG fluorescence image of the same area of skin, with the pixel values determined by the peak fluorescence value at each pixel. Higher ("hot") fluorescence intensity values 64 may indicate a higher ICG concentration or may be caused by perforator vessels located closer to the skin surface, which reduces absorption of the excitation light/fluorescence response. The vessels 66, 68 which were clearly visible in FIGS. 4 and 5, are barely distinguishable from the background.

While the images shown, for example, in FIGS. 2 and 6 are rendered with a linear contrast transfer function providing a 1:1 mapping of pixel values processed with the various algorithms described above to the displayed pixel intensities, images can also be rendered (as contour maps or false color overlays) with a variable contrast transfer function to enhance the visual differences in the image. In addition, labels may be placed in the overlay images, hereinafter referred to as ACR (accumulated or time-integrated intensity ratio) labels, which facilitate a quantitative comparison between two or more regions of the anatomy.

Because absolute pixel values in the image change when the dynamic range and slope of the variable contrast transfer function is modified, the ACR labels allow the user to compare the relative perfusion in different image regions as measured by any of the selected overlay techniques (e.g. accumulated/time-averaged intensity, etc.).

The following approach is used to compute the ACR label values. For clarity, we assume that accumulated intensity is selected as overlay technique, although the same approach can be used with any of the available overlay techniques.
1) The accumulated intensity for all pixels for all images in the image sequence is computed over a time window.
2) The accumulated intensity is averaged over a region of the selected label (for example, a 5×5 pixel square matrix).
3) The averaged intensity is normalized to the maximum value of the accumulated intensity in the entire image.
4) The normalized averaged is intensity scaled, with the maximum value of the transfer function representing 100%.

Figure 7:
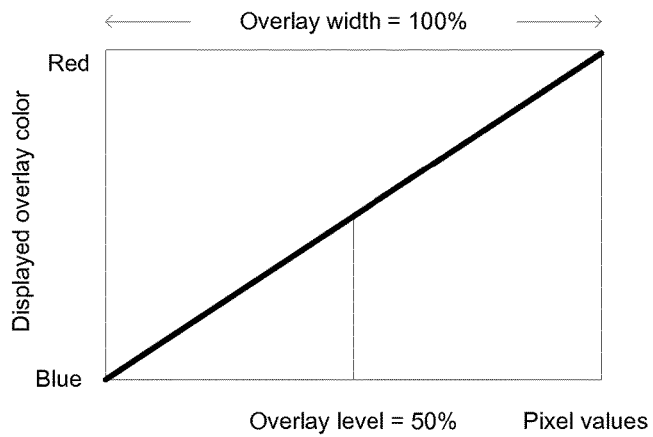
FIG. 7 shows an overlay of the fluorescence image processed with a variable contrast transfer function.
Figure 7:
Figure 8:
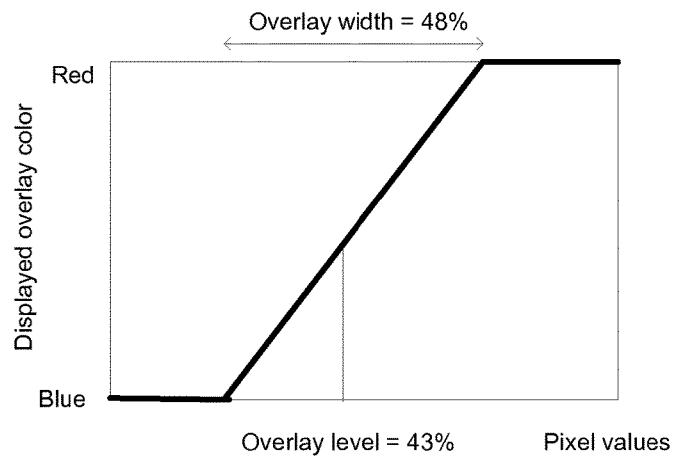
FIG. 8 shows an overlay of the fluorescence image processed with another variable contrast transfer function.
Figure 8:

By following this approach, the relative ratio of two different ACR labels remains unchanged even though the slope of the transfer function is modified. FIGS. 7 and 8 show a fluorescence image from the image sequence that has been processed with one of the aforementioned algorithms (upper part of the gray-scale image) and the false-color overlay image rendering the accumulated intensity from the sequence in color (from blue for low values to red for high values) for two different contrast functions. The pixel values in FIG. 7 are processed with a first contrast transfer function, giving two regions with 52% and 72% intensity, respectively, corresponding to a ratio of 52/72=0.72 between the two labeled regions. The second overlay image in FIG. 8 shows the same pixel values processed with a different contrast transfer function, with the intensity in the two regions now labeled 99% and 71%, respectively. However, their relative ratio remains essentially unchanged at 71/99=0.72.

The user can modify the transfer function so that a control region is labeled at 100%, wherein all other regions could then be compared to the control region.

Figure 9:
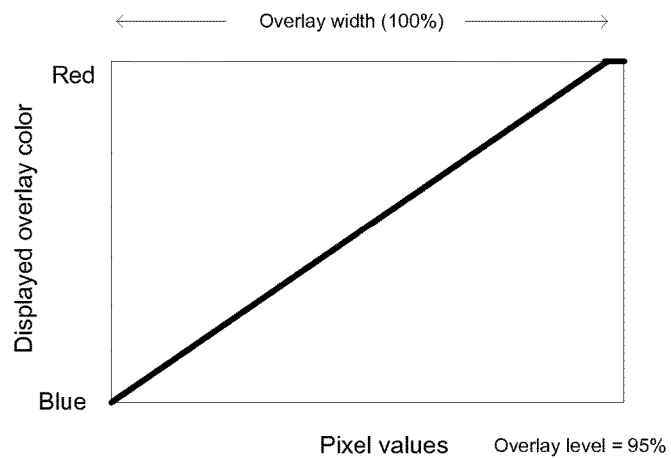
FIG. 9 shows an overlay of the fluorescence image processed with yet another variable contrast transfer function.
Figure 9:

FIG. 9 shows that the overlay is transparent where accumulated intensity pixels have a value less than the point where the bottom of the transfer function ramp intersects the horizontal pixel value axis. Further, this demonstrates that in this example 12% of the image area (Coverage number in the lower right of the bottom window) has accumulated intensity greater than 52% of the maximum accumulated intensity. The illustration shows several regions bounded by their 52% contours.

In the aforedescribed approach, the user could place labels on the image to compare relative perfusion of different tissue zones. These labels would normalize the accumulated intensity in a small region beneath the label to the accumulated intensity present in the zone at the top end of the color map range of interest. Although the value of individual labels would vary as the color mapping range was shifted, the ratios of the labels to one another would remain constant.

Practical trials have demonstrated that modifications in the aforedescribed methods would be desirable in order to better quantify the results and allow a more consistent comparison between profused areas.

Clinicians generally want to perform a consistent comparison of the perfusion of suspect tissue to that of well-perfused, "good" tissue. One way of doing that with the original technique described above is to go through the burdensome process of manually adjusting the color mapping range until a label placed on well-perfused tissue reaches 100%. This label may now be used as a "good" tissue reference.

Clinicians generally want to identify whether tissue which exhibits relative accumulated intensity at some percentage as compared to good tissue will suffer from necrosis. Inherent noise in the camera, variable conditions of illumination and surface reflectivity, and the presence of residual ICG in the patient make it difficult to ensure that the ratios are consistent.

Although the label ratios remained constant as the color mapping changed, clinicians found it confusing that the label values themselves vary in the process.

In one modified approach, two reference labels are placed on the image, either explicitly in a manual operation or implicitly through automatic computation as described below. The labels are denoted as the background or "0 Marker" and the reference or "100 Marker". Any additional labels placed on the accumulated intensity matrix are normalized to the range established by these markers.

Ideally, the "0 Marker" will be placed on native tissue outside the transplant flap. The accumulated intensity in a small region beneath this marker denotes background intensity that would result from background noise in the camera, possibly combined with signal from some residual ICG in the patient from prior acquisitions.

Using clinical judgment, the operator places the "100 Marker" on tissue that the clinician has identified as being well-perfused, "good" tissue. This establishes the "good" tissue reference.

The two markers now support direct normalized quantitative comparison of regions of perfusion on the flap.

Labels values are computed using the following formula:

$$L=100*(A_{label}-A_0)/(A_{100}-A_0),$$

where:
$A_{label}$ represents the accumulated intensity in the area beneath the label
$A_0$ represents the background accumulated intensity in the area beneath the "0 Marker"
$A_{100}$ represents the reference accumulated intensity in the area beneath the "100 Marker"

All existing and newly placed label values are now normalized to the range between the "0 Marker" and "100 Marker". Label values can exceed 100% and now do not change as the color mapping range is shifted for enhanced visualization.

Figure 10A:
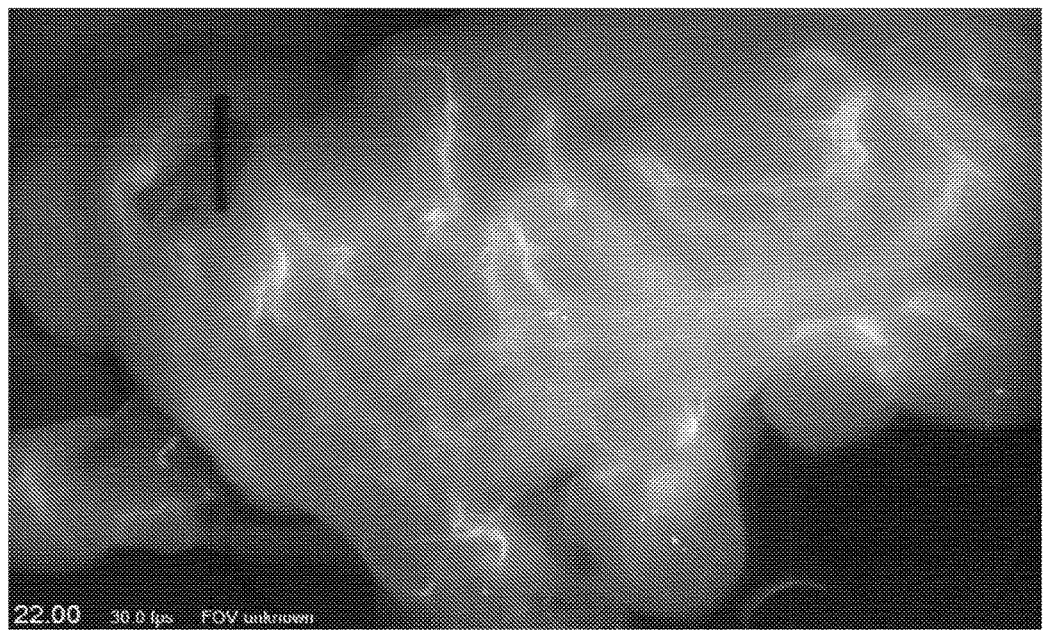
FIG. 10A is a fluorescence image of the perfused region.
Figure 10B:
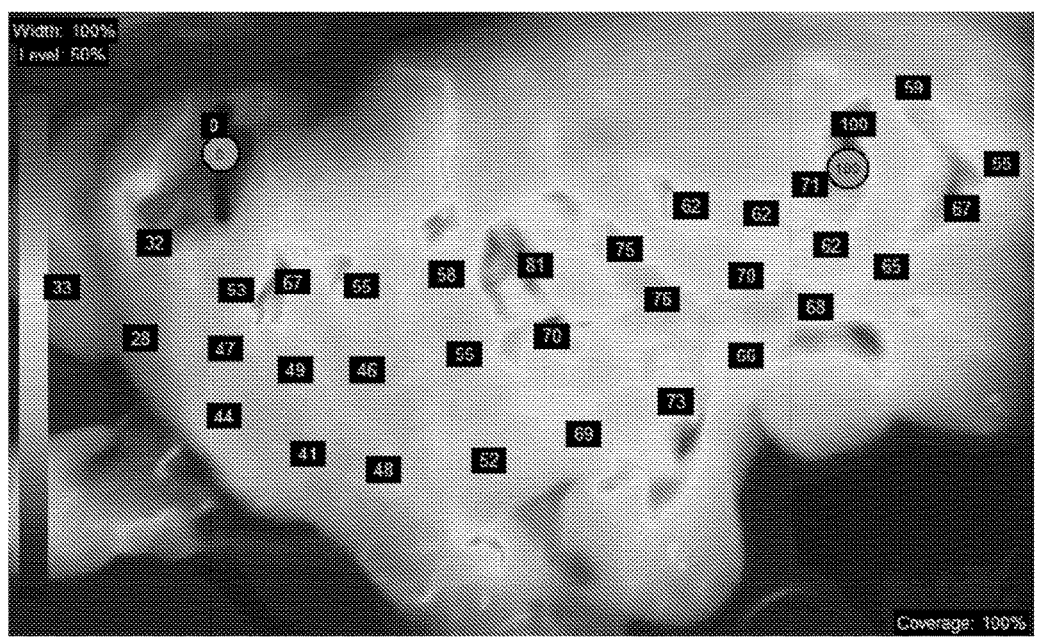
FIG. 10B is a black/white rendition of a colored overlay corresponding to the fluorescence image of FIG. 10A, with markers indicating a normalized intensity.

FIGS. 10A and 10B illustrate an exemplary embodiment of this technique. FIG. 10A is a fluorescence image of the perfused region, similar to those described above with reference to FIGS. 2 to 6. FIG. 10B is a black/white rendition of a colored overlay, with markers or label values computed with the formula:

$$L=100*(A_{label}-A_0)/(A_{100}-A_0).$$

The "0 Marker" is denoted in the upper left corner by the circle enclosing a "0" and the "100 Marker" is denoted in the upper right corner by the circle enclosing a "100". Because all areas of the tissue show some perfusion, the "0 Marker" has been placed on a surgical clip within the field of view.

The following are additional/alternative options for deriving values for the "0 Marker" or accumulated background intensity:

If no separate "0 Marker" is explicitly placed, a value for the "0 Marker" can be derived by averaging the accumulated intensity present in the first frame captured prior to the arrival of the ICG bolus. The average accumulated intensity is then computed by multiplying initial frame values by the number of frames in the sequence.

Alternatively, in the absence of a separate "0 Marker", a value for the "0 Marker" can be derived by first automatically determining what pixels represent tissue and then examining the first frame to compute the average background intensity only for those tissue pixels. The changing pixels are those which receive blood with ICG. To locate these tissue pixels, the software locates pixels whose intensity changes to exceed a predetermined threshold value. Unchanged pixels are disregarded.

A physical reference standard or patch with a known near-infrared reflectance may be placed in the field of view. Several of these physical patches would be provided to simulate different skin tones with known reflectance in the visual spectrum. The "0 Marker" could then be explicitly placed over these markers to approximate the accumulated intensity underneath the tissue that is not perfused with ICG-laden blood. This would allow normalization to different illumination conditions in the operating room.

In summary, labels can be used to easily compare different perfusion boundaries to the perfusion that is present in known good tissue. These labels now correct for the effects of residual ICG, camera noise, and other NIR scattering effects.

The described embodiments detect a fluorescence signal emitted transcutaneously by ICG following excitation in the near-infrared spectral range. However, those of skill in the art will appreciate that other dyes which can be excited and emit fluorescence in a spectral range where tissue transmits light can also be used.

While the present invention has been described with reference to an example of arterial blood flow, i.e. supply of blood to the perforator vessel(s), the method may also detect graft failure due to venous congestion by quantifying and displaying the rate of change from peak intensity back down to the baseline. This will highlight venous return in the perfusion area.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the appended claims.

We claim:

1. A method for evaluating tissue perfusion in a tissue of a subject, the method comprising:
   detecting, through a skin surface, a fluorescence response from the tissue arising from a bolus of ICG having been administered into the bloodstream of the subject;
   acquiring a temporal sequence of images of the fluorescence response over a period of time;
   independently processing each pixel in the temporal sequence of images of the tissue to (i) compute a temporally-based value for each pixel, wherein each temporally-based value is based on a plurality of images of the temporal sequence of images, and (ii) generate a spatial map of the computed temporally-based values; and
   displaying the spatial map of the computed temporally-based values,
   wherein each temporally-based value is a peak value of the fluorescence response for the respective pixel.

2. The method of claim 1, further comprising applying a contrast transfer function to the fluorescence response.

3. The method of claim 2, wherein the contrast transfer function represents a linear or nonlinear function which transforms the fluorescence response into an overlay image representing different perfusion characteristics in different colors.

4. The method of claim 3, further comprising displaying in the overlay image a zero ("0") marker representative of a background fluorescence response of (a) substantially unperfused tissue, (b) background noise, or (c) residual ICG and a hundred ("100") marker representative of a fluorescence response of well perfused tissue.

5. The method of claim 4, wherein the zero marker is associated with a non-fluorescent object placed on the substantially unperfused tissue.

6. The method of claim 4, wherein the zero marker is derived from a fluorescence response from tissue prior to arrival of the ICG bolus in the tissue.

7. The method of claim 4, further comprising displaying numerical values of the fluorescence response in the overlay image.

8. The method of claim 4, further comprising:
   normalizing the numerical values of the fluorescence response to a range between the zero marker and the hundred marker, and
   displaying normalized numerical values of the fluorescence response in the overlay image.

9. The method of claim 8, wherein the normalized numerical values of the fluorescence response are computed for different image regions of an anatomical feature.

10. The method of claim 9, wherein the normalized numerical values of the fluorescence response are computed with the following steps:
    computing the fluorescence response for all pixels,
    averaging the fluorescence response over a predefined region in the image,
    normalizing the averaged fluorescence response in the entire image, and
    scaling the normalized averaged fluorescence response of the contrast transfer function.

11. The method of claim 2, wherein the contrast transfer function is a non-linear function with regions of different slope, and wherein the different slopes and transition between the different slopes are adjusted during a procedure to evaluate the perfusion of the tissue.

12. The method of claim 1, further comprising:
    identifying a first reference label associated with native tissue apart from the tissue being evaluated;
    identifying a second reference label associated with fluorescence response of the tissue being evaluated that achieves a predetermined perfusion;
    normalizing at least one additional label associated with fluorescence response of pixel values for a second region of the tissue being evaluated to the range established by the first and second reference labels; and
    displaying the first reference label, the second reference label, and the at least one additional label on a color or black-and-white image.

13. The method of claim 12, wherein the first reference label, the second reference label, and the one additional label are each numerical values.

14. The method of claim 1, further comprising:
    selecting a zone from the tissue being evaluated for use in a subsequent surgical step based on the spatial map of the computed temporally-based values.

15. The method of claim 1, further comprising:
    determining a zone from the tissue being evaluated for use in reconstructive surgery based on perforator vessels in the tissue being evaluated represented in the spatial map of the computed temporally-based values.

16. The method of claim 1, further comprising:
    selecting, in the temporal sequence of images or in the spatial map, a target region, a first reference region representing a well-perfused tissue, and a second reference region representing background, and
    processing the target region using the first reference region and the second reference region to compute a quantitative representation of tissue perfusion in the target region.

17. The method of claim 1, further comprising:
    generating in real time a composite overlay image of the fluorescence response.

18. An apparatus for evaluating perforator vessels in candidate perforator flaps, comprising:
    means for detecting a fluorescence response from blood-carried ICG in the perforator vessels in the candidate perforator flaps;
    means for acquiring a temporal sequence of images of the fluorescence response over a predetermined time;
    means for processing the sequence of images to yield a time-integrated intensity or time-derivative of the intensity for pixel values in the images corresponding to the blood-carried ICG in the perforator vessels in the candidate perforator flaps, said means for processing including an algorithm that inversely weights the pixel values in relation to elapsed time from application of an ICG bolus into the bloodstream until fluorescence; and
    means for displaying the time-integrated intensity or time-derivative of the intensity as a color or black-and-white image.

19. An apparatus for evaluating tissue perfusion in a tissue of a subject, comprising:
    a camera configured to detect, through a skin surface, a fluorescence response from the tissue arising from a bolus of ICG having been administered into the bloodstream of the subject;
    a processor configured to
    acquire a temporal sequence of images of the fluorescence response over a period of time, and
    independently process each pixel in the temporal sequence of images of the tissue to (i) compute a temporally-based value for each pixel, wherein each temporally-based value is based on a plurality of images of the temporal sequence of images, and (ii) generate a spatial map of the computed temporally-based values; and a display configured to display the spatial map of the computed temporally-based values, wherein each temporally-based value is a peak value of the fluorescence response for the respective pixel.

20. The apparatus of claim 19, wherein the processor is further configured to select, in the temporal sequence of images or in the spatial map, a target region, a first reference region representing a well-perfused tissue, and a second reference region representing background, and process the target region using the first reference region and the second reference region to compute a quantitative representation of tissue perfusion in the target region.

* * * * *